(12) United States Patent
Johnson et al.

(10) Patent No.: US 6,993,170 B2
(45) Date of Patent: Jan. 31, 2006

(54) METHOD FOR QUANTITATIVE ANALYSIS OF BLOOD VESSEL STRUCTURE

(75) Inventors: Peter C. Johnson, Pittsburgh, PA (US); Mary Del Brady, Pittsburgh, PA (US); Michael G. Fuhrman, Pittsburgh, PA (US); Othman A. Abdul-Karim, Pittsburgh, PA (US); Sujal Shah, Pittsburgh, PA (US)

(73) Assignee: Icoria, Inc., Research Triangle Park, NC (US)

( * ) Notice: Subject to any disclaimer, the term of this patent is extended or adjusted under 35 U.S.C. 154(b) by 0 days.

(21) Appl. No.: 10/041,254

(22) Filed: Jan. 7, 2002

(65) Prior Publication Data

US 2002/0086347 A1 Jul. 4, 2002

Related U.S. Application Data

(63) Continuation-in-part of application No. 09/338,904, filed on Jun. 23, 1999, now abandoned, and a continuation-in-part of application No. 09/338,908, filed on Jun. 23, 1999, now Pat. No. 6,581,011, and a continuation-in-part of application No. 09/338,909, filed on Jun. 23, 1999, now Pat. No. 6,611,833.

(60) Provisional application No. 60/259,822, filed on Jan. 5, 2001.

(51) Int. Cl.
*G06K 9/00* (2006.01)

(52) U.S. Cl. ................... 382/128; 702/19; 702/21; 382/130; 382/131; 382/132; 382/133; 382/134; 382/190; 382/191; 382/192; 382/193; 382/194; 382/195; 382/256; 382/257; 382/266

(58) Field of Classification Search ............... 702/19, 702/21; 382/128, 130–134, 190–195, 256–257, 382/266
See application file for complete search history.

(56) References Cited

U.S. PATENT DOCUMENTS

| | | | |
|---|---|---|---|
| 5,784,162 A | 7/1998 | Cabib et al. ............... 356/346 |
| 5,974,201 A * | 10/1999 | Chang et al. ............... 382/305 |
| 6,101,265 A | 8/2000 | Bacus et al. ............... 382/133 |
| 6,137,899 A | 10/2000 | Lee et al. ............... 382/133 |
| 6,181,811 B1 | 1/2001 | Kuan et al. ............... 382/133 |
| 6,246,785 B1 | 6/2001 | Molnar et al. ............... 382/133 |
| 6,264,609 B1 * | 7/2001 | Herrington et al. ......... 600/443 |
| 6,404,906 B2 | 6/2002 | Bacus et al. ............... 382/128 |
| 6,415,046 B1 | 7/2002 | Kerut, Sr. ............... 382/128 |
| 6,463,438 B1 | 10/2002 | Veltri et al. ............... 707/15 |
| 6,520,981 B1 * | 2/2003 | LaMuraglia ............... 607/89 |

* cited by examiner

*Primary Examiner*—Marianne P. Allen
(74) *Attorney, Agent, or Firm*—Icoria, Inc.

(57) ABSTRACT

We disclose quantitative geometrical analysis enabling the measurement of several features of images of tissues including perimeter, area, and other metrics. Automation of feature extraction creates a high throughput capability that enables analysis of serial sections for more accurate measurement of tissue dimensions. Measurement results are input into a relational database where they can be statistically analyzed and compared across studies. As part of the integrated process, results are also imprinted on the images themselves to facilitate auditing of the results. The analysis is fast, repeatable and accurate while allowing the pathologist to control the measurement process.

5 Claims, 24 Drawing Sheets

METHOD FOR QUANTITATIVE ANALYSIS OF BLOOD VESSEL STRUCTURE

This application claims the benefit of U.S. Provisional Application No. 60/259,822 filed Jan. 5, 2001, and is a continuation-in-part of U.S. application Ser. No. 09/338,904 filed Jun. 23, 1999, now abandoned. U.S. application Ser. No. 09/338,909 filed Jun. 23, 1999, now U.S. Pat. No. 6,611,833, issued Aug. 26, 2003, and U.S. application Ser. No. 09/338,908 filed Jun. 23, 1999, now U.S. Pat. No. 6,581,011, issued Jun. 17, 2003. The contents of the U.S. applications Ser. No. 09/338,904, Ser. No. 09/338,909 and Ser. No. 09/338,908 are incorporated herein by reference in their entirety.

FIELD OF THE INVENTION

The present invention generally relates to characterization of tissue for the creation of images and associated data ("tissue information") suitable for a robust, relational database that manages the input and retrieval of such information needed to perpetuate the tissue information for comparison and combination with tissue information obtained through studies taking place at different times, with different protocols and with measurements made by different systems.

BACKGROUND OF THE INVENTION

Accurate and repeatable quantitative analysis of tissue is important to characterize the progression of various pathologies, and to evaluate effects that new therapies might have. To date, little if any reliable structural information exists at the tissue level (1–1000 microns, that is, in the range microscopic to mesoscopic). It is believed that if reliable, multi-dimensional tissue structural information existed in readily accessible databases capable of continuous assimilation with newly acquired information, including clinical and molecular (including genetic) information, such information would serve to enhance and accelerate new advances in tissue engineering, drug design, gene discovery, proteomics, and genomics research.

The present invention overcomes the problems of the current art. Present visual/manual analysis of tissue is slow, difficult, and prone to error. The present invention eliminates manual zooming and panning at several resolution scales to establish relevant tissue features. Disclosed herein are image processing and analysis methods to automate feature extraction from tissue and to enable an objective, quantitative definition of tissue geometry. Measurement results are input into a relational database where they are statistically analyzed and compared across studies.

In particular, the present invention provides a capacity to visualize and quantitatively analyze different structural elements of a given tissue which are otherwise difficult to visualize, and quantitate accurately and efficiently. The present invention is also efficient over prior art known methods in that the time required for the geometrical analysis of a given tissue or organ is reduced by several fold. For example, one skilled in the art can accurately analyze 30–40 tissue specimens in about 3 hours by practicing the present invention.

SUMMARY OF THE INVENTION

The present invention is directed to a method to facilitate visualization of a feature in a tissue specimen comprising one or more of the steps of obtaining an image of a tissue specimen; using objectively defined criteria to locate a feature of interest in the image; using mathematical algorithms to construct boundaries of the feature; and using objectively defined criteria to establish self-consistency.

Objectively defined criteria include knowledge of color, intensity of the color, and the morphology of the feature in the tissue specimen. As to color, stains which are specific to a certain material can create objectively defined criteria. For example, elastin can be stained to appear dark blue and collagen can be stained to appear red. Size and shape can create objectively defined criteria. In the case of images of blood vessels as in FIGS. 1A and 1B the large open area can be recognized either by computers or human operators as the lumen. Color, intensity, and morphology can be combined to create objectively defined criteria. For example, the very long thin darkly stained object that is approximately four microns across and just outside the lumen is the internal elastic lamina. Connectivity can create objectively defined criteria. For example, the internal elastic lamina may be broken in one or more plates. Either computers or human operators can identify the fractured ends of the internal elastic lamina. Separately, sequences of features can create objectively defined criteria. For example, muscle tissue may be growing in between the lumen and the internal elastic lamina because of damage to the vessel. In a pig, the tunicia adventia can look like it is peppered with dark spots of elastin and encircles the vessel.

Mathematical algorithms are used to construct boundaries of a feature. Algorithms for morphological operations can include dilation (adding pixels to the boundary of an object) and erosion (removing pixels on the object boundaries). The number of pixels added or removed depends on the size and shape of the structuring element used to process the image. Thresholding, the turning of pixels completely on or off depending on whether the value is above or below a threshold, is also used. In the case of blood vessels, algorithms are used to provide functions to remove all islands of tissue inside of the lumen (a fill operation) and to provide coordinates of pixels on the boundary of the lumen.

Embodiments of algorithms of the present invention include the following. In the example of blood vessels, capturing an image from off to the side where there is no tissue in order to measure the background intensity. We assume the lumen is just as bright, and that the lumen will be the largest bright object completely surrounded by tissue. Separately, by taking advantage of knowledge that the adventitia has a certain color and shape, we use a structuring element of a certain size, and perform dilation and erosion operations repeatedly so that the adventitia remains as all other colors and shapes are made to disappear. The purpose of the image processing is to connect all the small dark strands of elastin into one large object. The size of the structuring element, and the number of iterations need to be sufficient to connect the small objects into one large object. A person of ordinary skill in the field would look at the images at the captured image resolution, to visually determine the average spacing between small dark objects in order to determine the structuring element and number of iterations to connect the objects. Separately, by taking advantage of knowledge that the internal elastic lamina has a certain color and shape, we use a structuring element of a certain size and perform dilation and erosion operations repeatedly so that the internal elastic lamina remains as all other colors and shapes are made to disappear. In addition one takes advantage of proximity relations; the internal elastic lamina has to be between the lumen and the adventitia, so the image processing operations and the search for the internal elastic lamina only takes place within this region. All objects outside the region are made to disappear by default.

In the embodiment of algorithm using threshold and morphological operations, the inputs to the algorithm are a threshold, the shape of the structuring elements (which are the size of the feature of interest), and the number of iterations (which depends on the distances between features of interest). One can threshold the image to find the bright lumen among many smaller objects and choose the largest bright object found in the image to be the lumen, as long as this object is completely contained within the tissue (that is, as along as this object doesn't touch the edge of the image.) One can apply a morphological filter that enhances small dark objects that are about four microns across (like the internal elastic lamina) and suppress the visibility of other features. One can then locate all small dark objects that are close to each other and connect them. Closeness determines the number of iterations of dilation or erosion. This can create many objects that look like chains in the image, but one or more of them are quite long. These long objects comprise the internal elastic lamina. One can continue to locate and connect small dark objects that are further and further away from each other and thereby large objects are created (with the largeness depending on the number of iterations). The largest object is the adventitia. The inside edge of the adventitia, as viewed from the lumen, is the external elastic lamina.

The algorithms can be implemented with or without intervention of a human operator. As an example, consider blood vessel analysis. The computer itself can utilize color, intensity, and morphology criteria to identify features. For example, one of the primary components of the adventitia is elastin, so the adventitia has a higher density of elastin than other areas of tissue comprising and surrounding the blood vessel. The image of the vessel can be processed to find the density of elastin throughout the image, and the spacing between elastin stained objects throughout the image. The average shape and average spacing between elastic objects in the regions of highest elastin density can be used as parameters to automatically set the size and shape of the structuring element, and the upper limit on the number of iterations used, to find the adventitia. Similarly, the internal elastic lamina is comprised of elastin. The internal elastic lamina exists between the lumen and the adventitia. The structuring element used takes advantage of the observation that the internal elastic lamin is approximately 4 microns across.

Objectively identified criteria can be used to establish the self-consistency of the construction of boundaries. These objectively identified criteria can include information on color, intensity, morphology, connectivity, or sequencing. For example, in the case of blood vessels, one can assume that damage to the vessel is such that a lumen, adventitia, and internal elastic lamina exist and are located in a certain order. Analysis results can be overplayed on the image for review by a pathologist. The overlay can be visually enhanced to enable quick review and modification.

The present invention is further directed to a method for quantitative determination of geometry of a given blood vessel comprising one or more of the following steps: imaging a cross section of the given blood vessel to create an image of the blood vessel; extracting features of the image to identify different boundary segments based on intensity, color, and morphology of the image; applying image processing algorithms and computing boundary segment perimeters and areas after step (b); and determining the blood vessel geometry based on the bound segment perimeters and areas.

The present invention is further directed to a method for rapidly localizing a fractured boundary segment in a blood vessel image and generating a contour connecting the fractured ends, the method comprising one or more of the following steps: processing a cross section of the blood vessel defining a target for imaging; imaging the target to capture an image of the entire target; identifying different boundary segments including the fractured boundary segment by using an image processing algorithm; computing boundary segment perimeters and areas after step (c); and generating a contour connecting the fractured ends based on the boundary segment perimeters and areas.

The present invention is further directed to a database that includes characterization data and/or associated images ("tissue information") representative of a tissue population, an automated method to create such database, and the use of the database for classification and evaluation of tissue specimens. In a method of the present invention, samples of normal tissue specimens obtained from a subset of a population of subjects with shared characteristics are profiled in order to generate a plurality of structural indices that correspond to statistically significant representations of tissue associated with the population. The structural indices include cell density, matrix density, blood vessel density, and layer thickness or geometry.

In a further embodiment of the present invention, samples of specimens of a particular tissue obtained from a subset of a population of subjects are profiled with respect to certain structural or other indices that correspond to relevant clinical conditions associated with that tissue to perpetuate the information obtained in a form and manner which provides for the comparison or combination of that information with information obtained from additional specimens of the tissue, including specimens which may have been previously profiled by other means or for other purposes.

The present invention is also directed to a method for classifying tissue specimens, comprising the steps of capturing images of the tissue specimens, identifying features within the tissue specimens, measuring parameters associated with the features of the tissue specimens and storing said parameters, wherein a plurality of the steps are automated.

In a particular embodiment, the invention is directed to an accurate and repeatable analysis of the shape of components of blood vessels. Methods are disclosed to enable a measurement and analysis system to quantitatively evaluate blood vessel geometry while reducing the tedium involved in making manual measurements. The steps of the automated method involve capturing images, assembling images, highlighting features, identifying boundaries of the features, and placing results and images into a database for easy retrieval and statistical analysis.

BRIEF DESCRIPTION OF THE DRAWINGS

The present invention and its presently preferred embodiments will be better understood by way of reference to the detailed disclosure hereinbelow and to the accompanying drawings, wherein.

DETAILED DESCRIPTION OF THE INVENTION

Figure 1A:
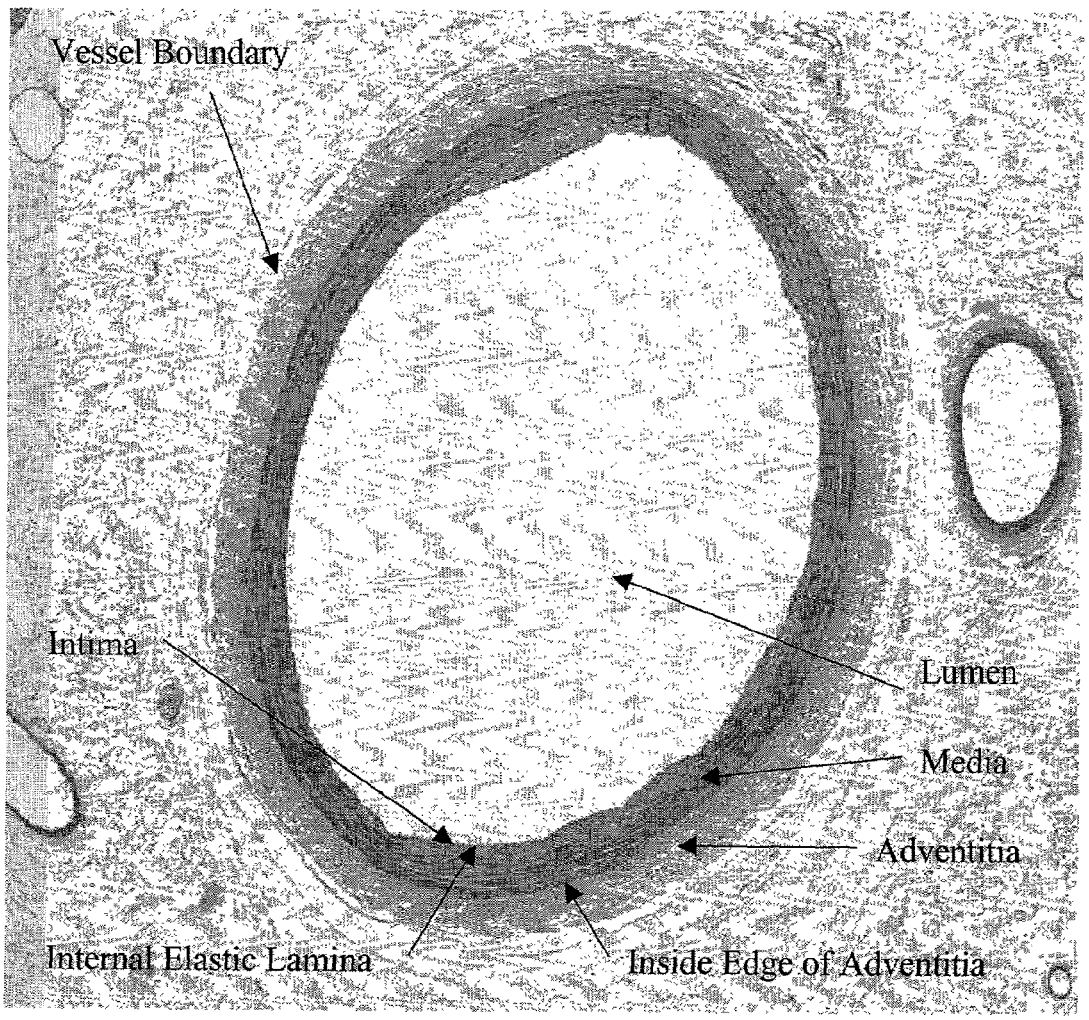
FIGS. 1A and 1B show Images of cross section of normal artery (FIG. 1A) and an artery showing fractured the internal elastic lamina (IEL) and a curve connecting the fractured ends (FIG. 1B).

In the Applicant's co-pending U.S. patent application Ser. No. 09/338,904, Ser. No. 09/338,909 and Ser. No. 09/338,908, novel databases having structural, cell function and/or mechanical indices that correspond to statistically significant representations of tissue characteristics are disclosed The present invention relates to a novel approach to an automated measurement and analysis system to quantitatively evaluate tissue structural indices and shape of tissue specimens (for example, cross sections of tissues or organs). The tissue specimens that can be analyzed by the present invention include liver, kidney, bile duct, gastrointestinal tract, lymphatic vessel, bronchia and blood vessels. The section (e.g., cross section) of a given tissue specimen does not necessarily exclude the presence of tissue that is naturally present surrounding the given tissue specimen under study. For example, blood vessels are present in muscle tissue. A cross section of a given blood vessel from muscle tissues may include the muscle tissue surrounding the blood vessel (i.e., a cross section showing blood vessel tissue within muscle tissue). Therefore, reference to phrases such as, for example, a cross section of a blood vessel shall not be construed to mean only the blood vessel tissue and no other tissue is present in that cross section. The surrounding tissue may or may not be quantitatively analyzed. The present invention reduces the tedium involved in making manual measurements. The practice of the present invention will employ histochemistry, microscopy, imaging and computer software all within the skill of the art.

The present invention employs certain objectively defined criteria to visualize features of interest in an image and employs algorithms for quantitative characterization of these features.

The present invention is also directed to a robust database that is based upon input parameters that may be uniformly investigated and extracted from different studies. The present invention is directed to a database that allows input and retrieval of data and images needed to compare studies taking place at different times, with different protocols, and with measurements made by different systems. The present invention is directed to a database which preserves the utility of the stored information through continued lossless combination and comparability with subsequently acquired information and the accessibility of the stored images for automated re-analysis.

Embodiment of Blood Vessel Measurement

Re-narrowing or restenosis of a human coronary artery occurs within six months in one third of balloon angioplasty procedures. Accurate and repeatable quantitative analysis of vessel shape is important to characterize the progression and type of restenosis, and to evaluate effects new therapies might have. A combination of complicated geometry and image variability, and the need for high resolution and large image size makes visual/manual analysis slow, difficult, and prone to error. The image processing and analysis described here was developed to automate feature extraction of the lumen, internal elastic lamina, neointima, external elastic lamina, and tunica adventitia and to enable an objective, quantitative definition of blood vessel geometry. The quantitative geometrical analysis enables the measurement of several features including perimeter, area, and other metrics of vessel damage. Automation of feature extraction creates a high throughput capability that enables analysis of serial sections for more accurate measurement of restenosis dimensions. Measurement results are input into a relational database where they can be statistically analyzed and compared across studies. As part of the integrated process, results are also imprinted on the images themselves to facilitate auditing of the results. The analysis is fast, repeatable and accurate while allowing the pathologist to control the measurement process.

Background of Blood Vessel Embodiment

Accurate and repeatable analysis of the shape of blood vessels is important to a variety of researchers for several reasons. Geometrical analysis is required to determine the extent of damage caused by atherosclerotic plaques, to determine the progression of restenosis and the formation of aneurysms, to determine the consequences of novel drug or device therapeutics on blood vessel structure, and to aid in the design and manufacture of engineered blood vessels. Software tools to characterize the geometry of blood vessels and to automate the analysis and archiving of the extracted information have been developed. The measurement process that will be described was developed using images of porcine vessels exhibiting restenosis-like response to balloon angioplasty.

Figure 1B:
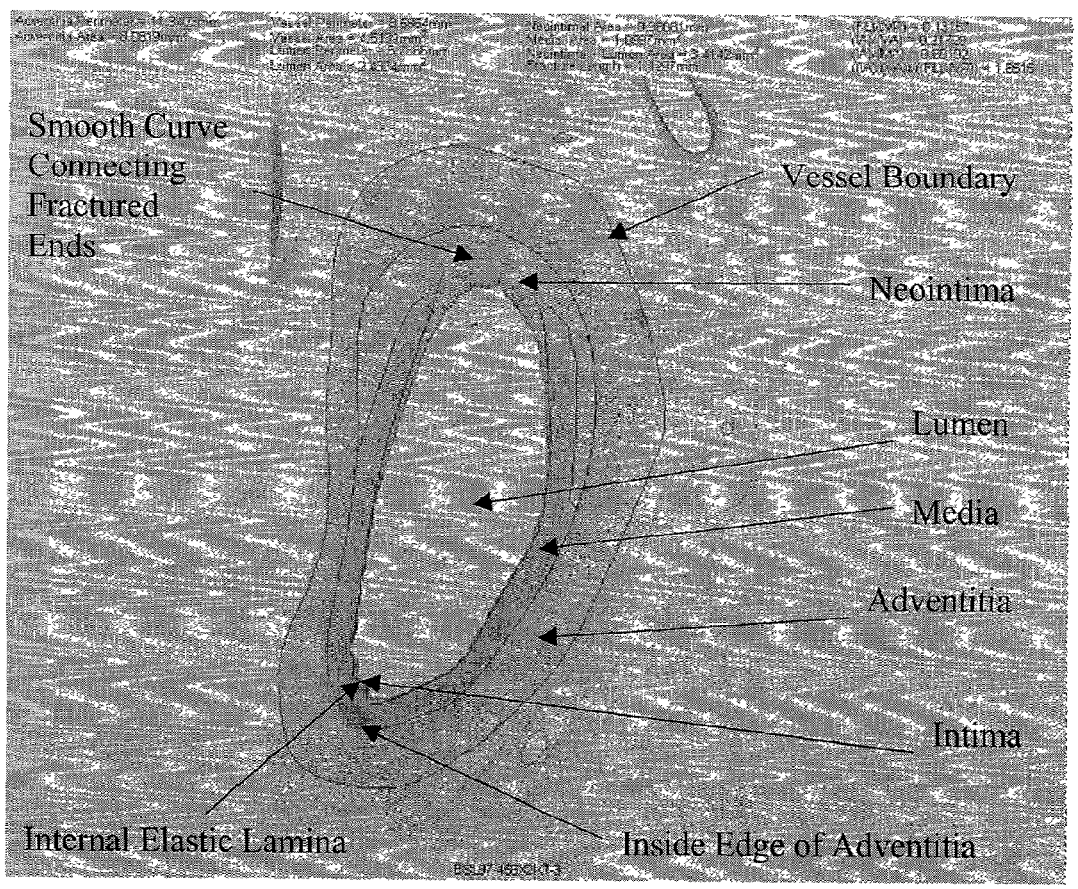
Figure 2A:
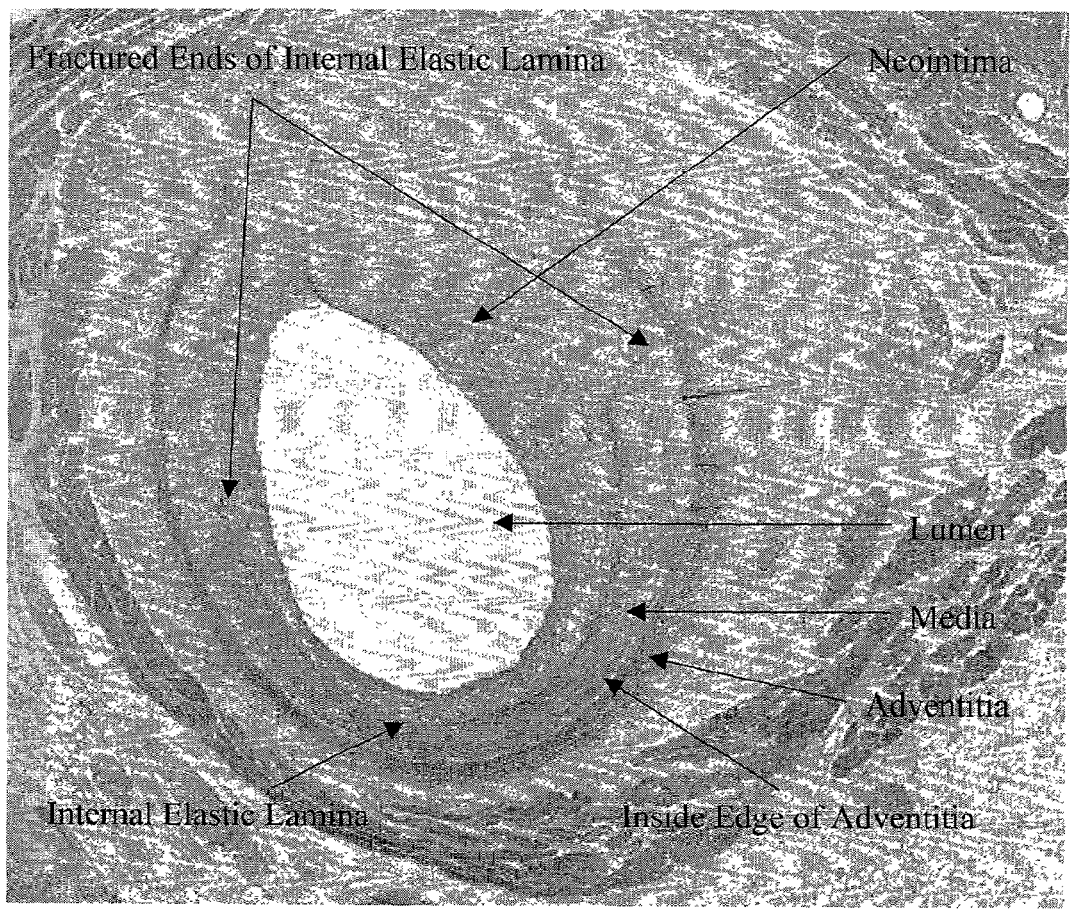
FIGS. 2A–2H illustrate an assortment of blood vessel images showing range of variability in vessel geometry.
Figure 2B:
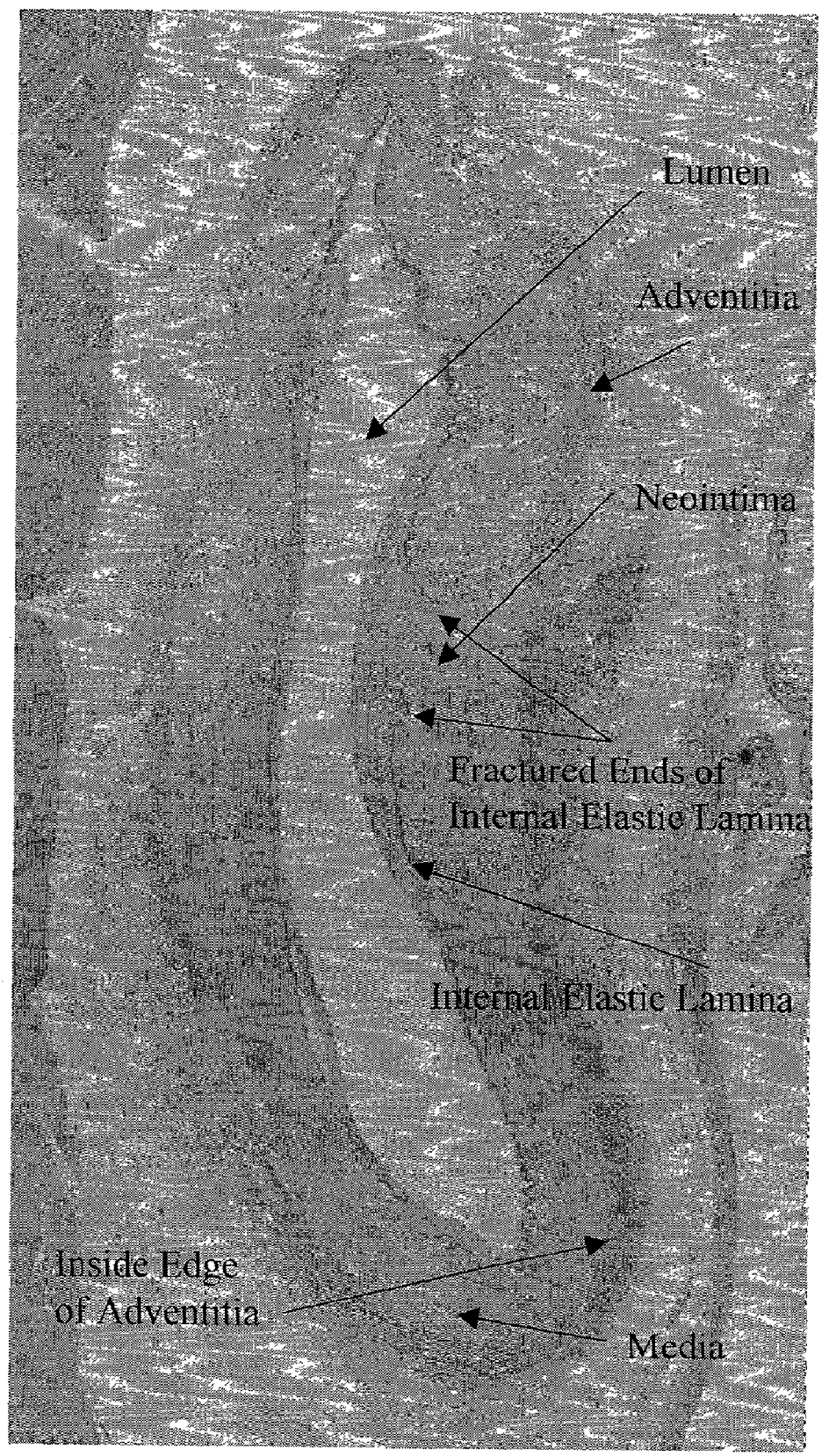
Figure 2C:
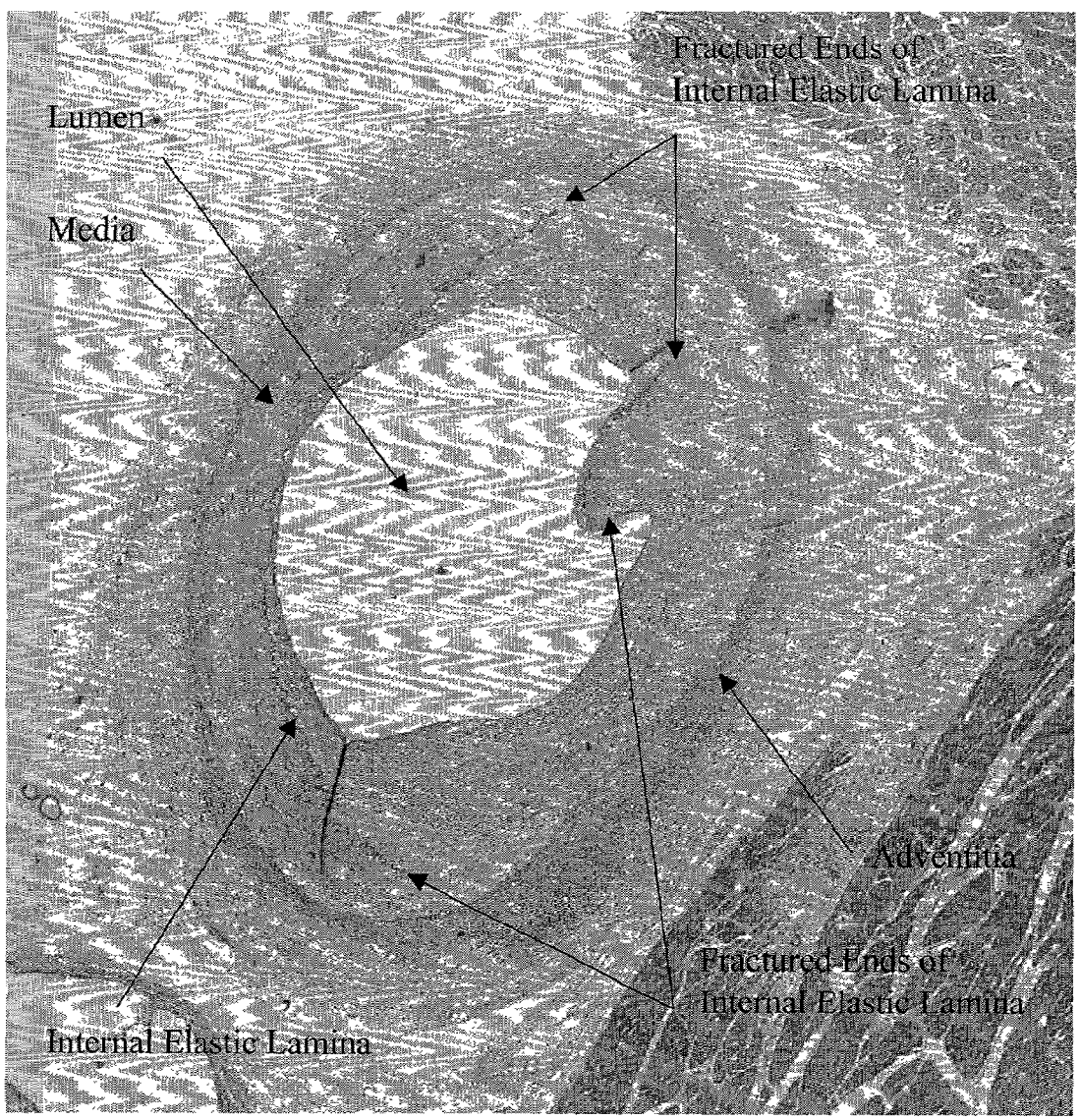
Figure 2D:
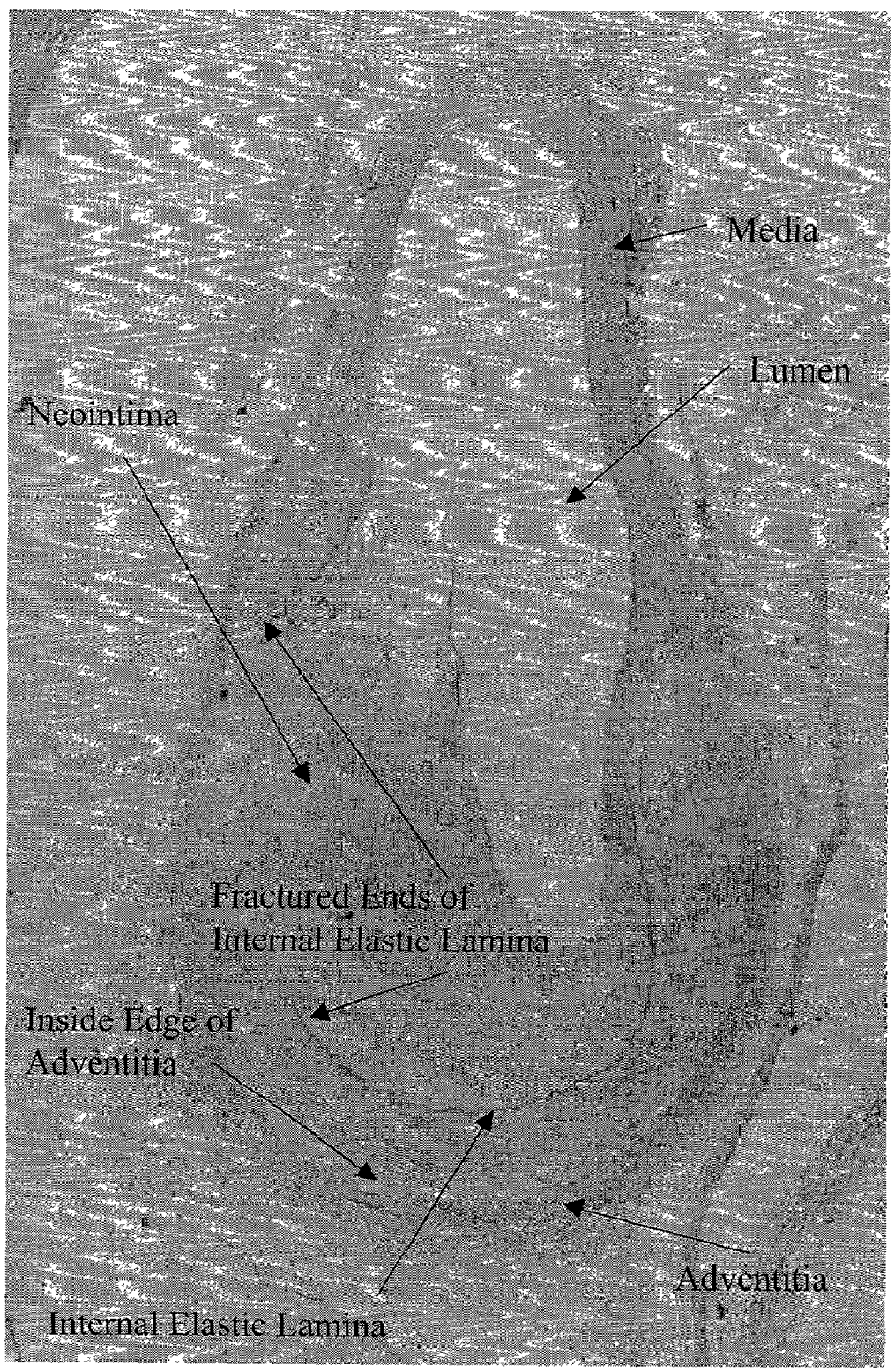
Figure 2E:
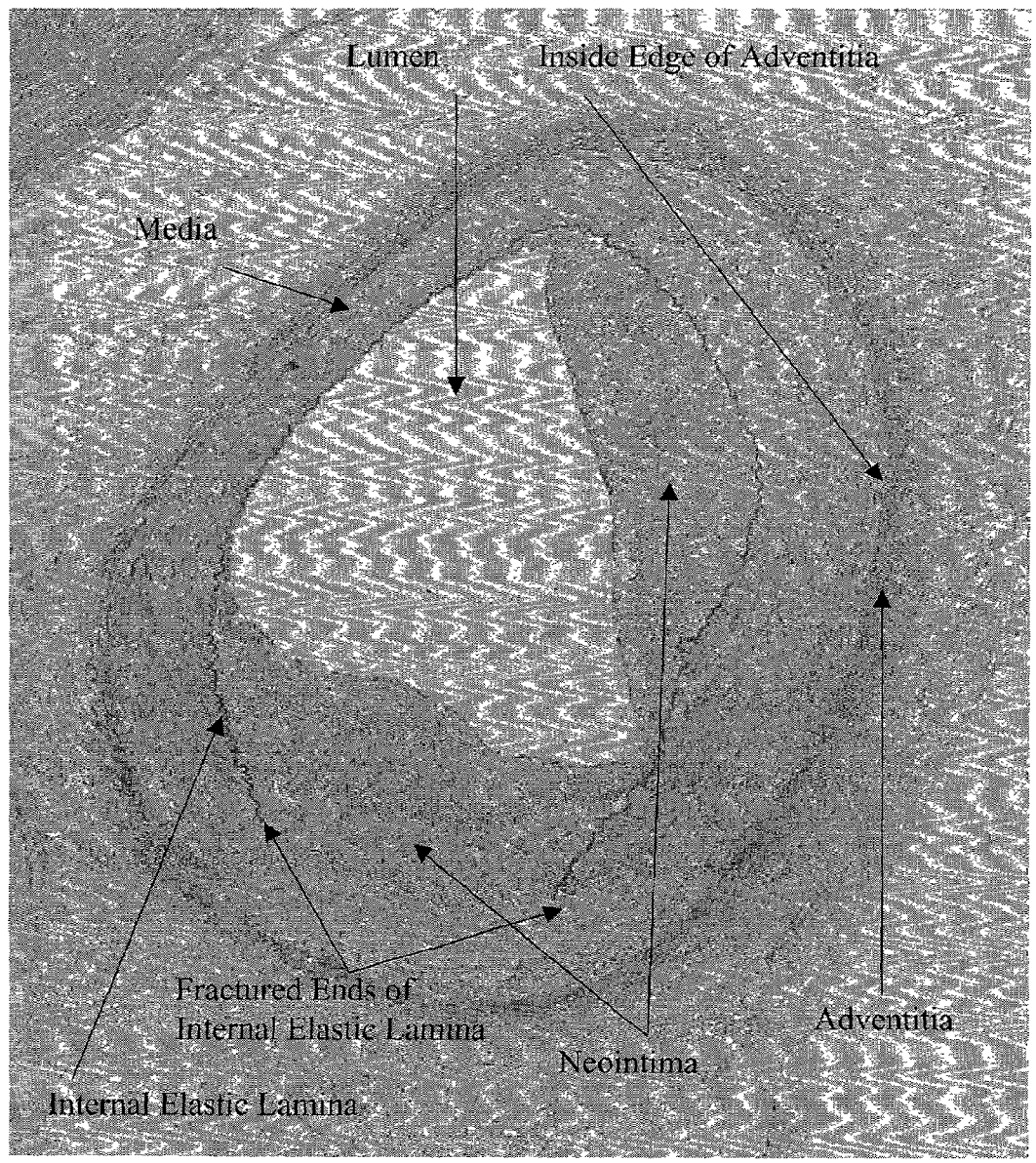
Figure 2F:
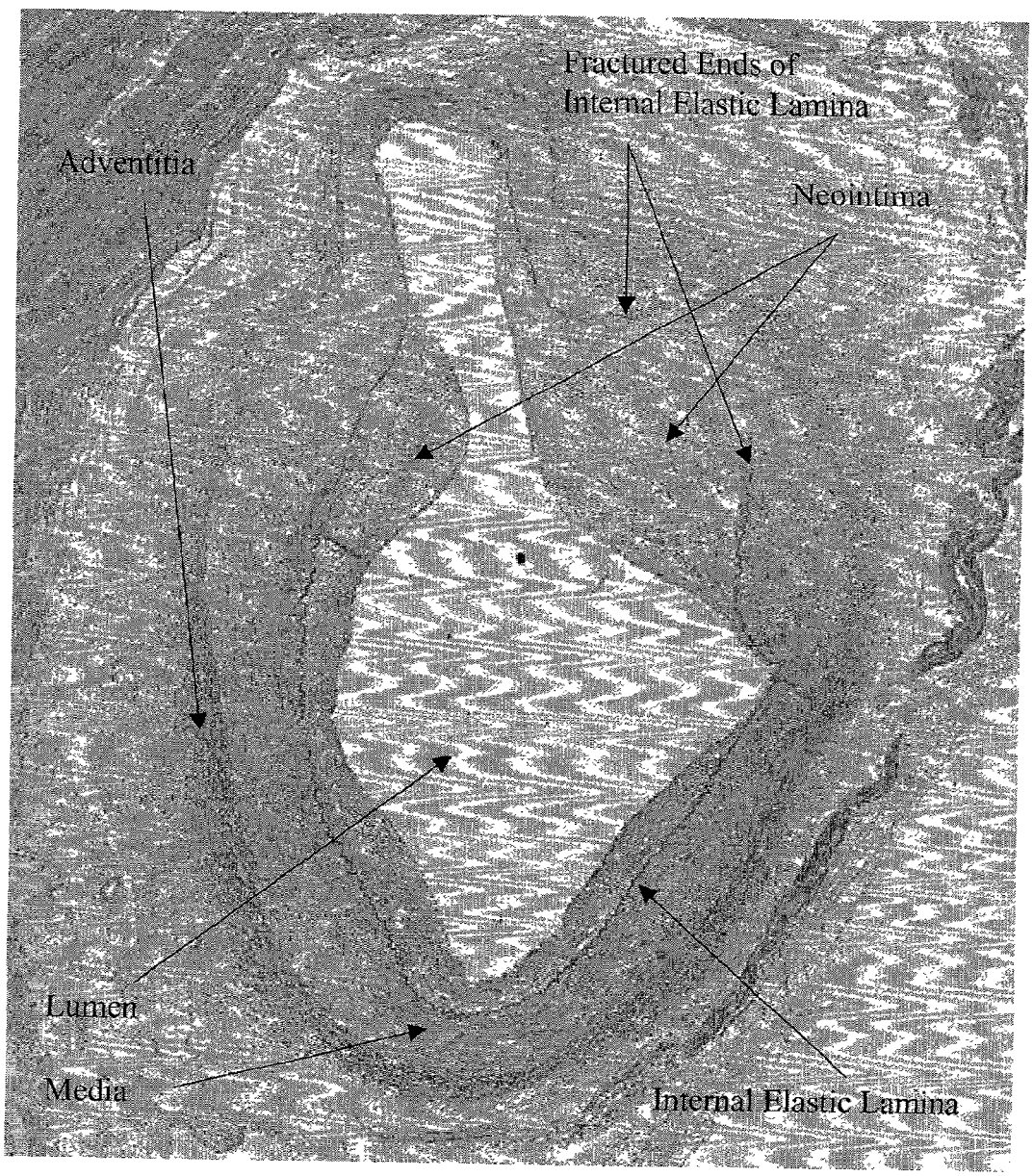
Figure 2G:
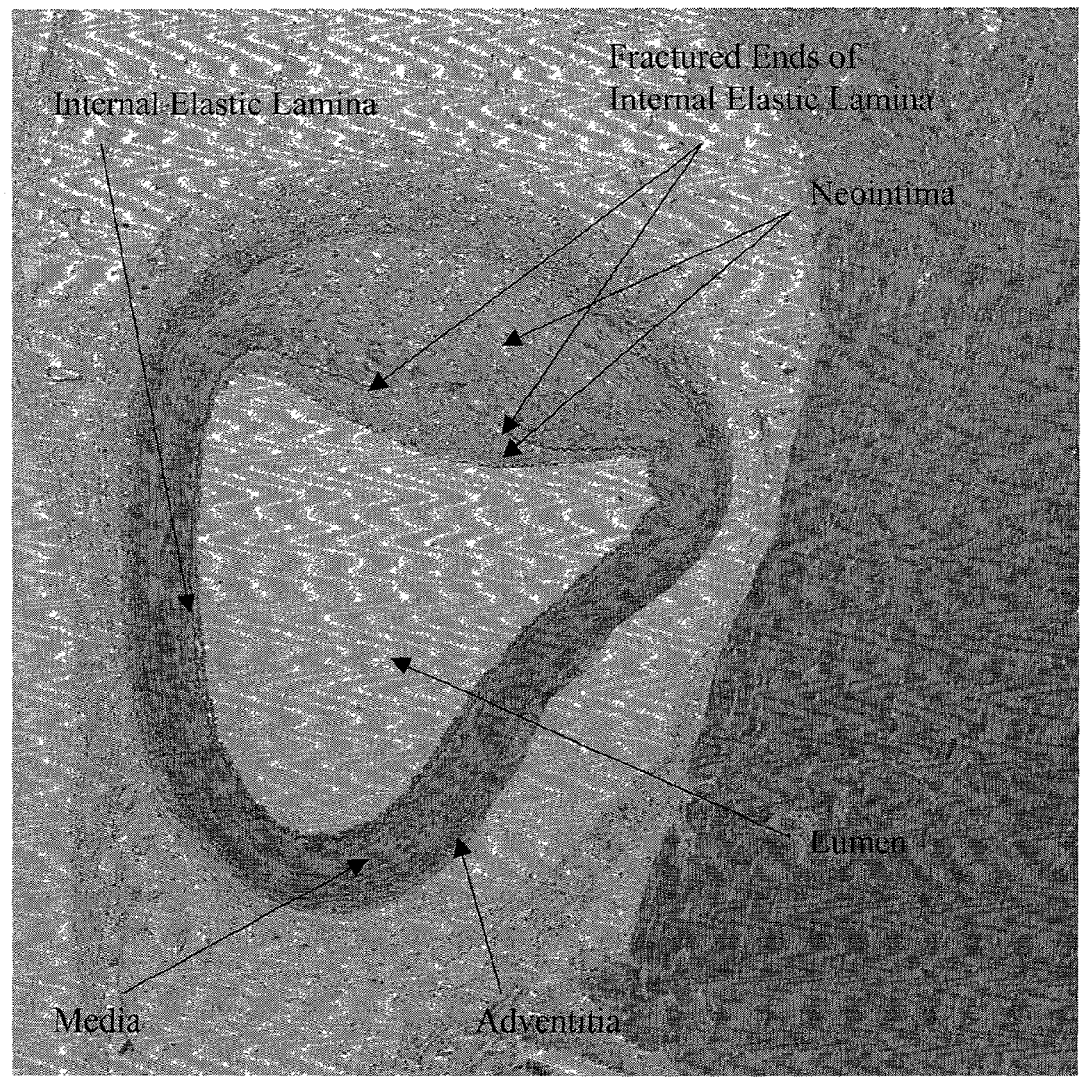
Figure 2H:
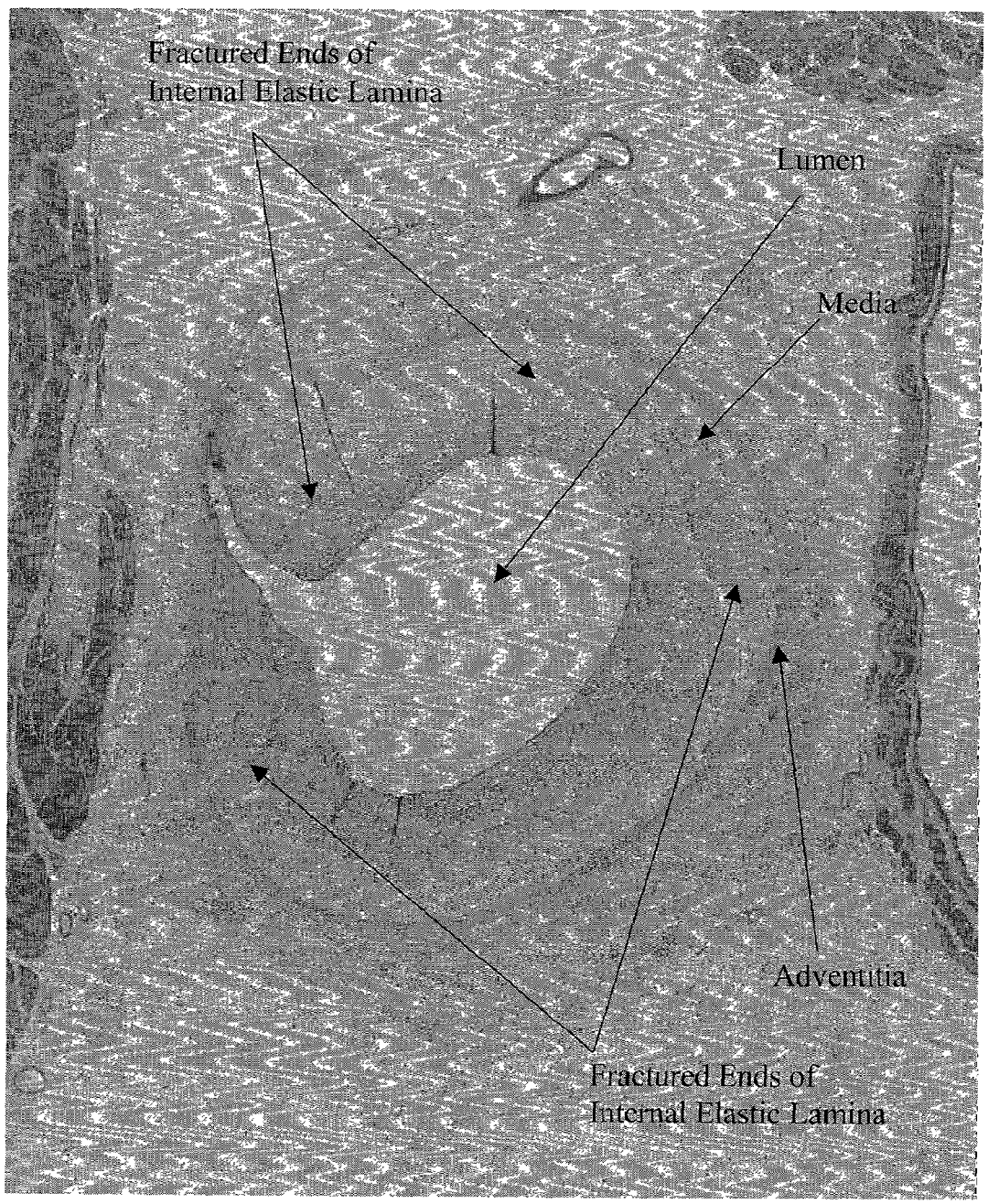

Types and basic structure of a blood vessel are known in the art. Types of blood vessels include arteries and veins. Blood vessel geometry refers to the overall shape of the blood vessel and the spatial relationship of different structures within the blood vessel. FIGS. 1A and 1B highlight the different features that will be discussed. These include the lumen, internal elastic lamina (IEL), external elastic lamina (EEL), tunica intima, neointima, tunica media, and tunica adventitia. The term boundary segment as used herein refers to structures such as IEL, EEL, tunica intima, tunica media, or tunica adventitia.

Manually outlining the contours of feature boundaries of dozens of vessel specimens a week is a very tedious process. Given the variability of blood vessel shape, the manual process cannot be replicated exactly from one time to the next simply because the boundaries are not smooth and will be drawn differently each time. The process is similar to tracing the boundary of a shoreline on a map while deciding whether to outline every small inlet. The diameter of a vessel can span hundreds of microns, while micron resolution is required to detect and outline features such as the internal elastic lamina. As a result, vessel geometry must be analyzed at several resolution scales requiring zooming and panning across an image.

Two other time-consuming parts of the process include calculating the required parameters and archiving the results in a way that they can be easily retrieved along with the images. Image processing algorithms are capable of identifying and computing boundary perimeters and areas, both with and without manual intervention. However, more effort is needed to determine whether there is any detectable difference between various treatments for restenosis. As will be seen, there is variability in the shape of injured vessel cross sections. The data needs to be organized and retrievable both for audit and statistical analysis.

Since the measurements may not completely characterize vessel geometry, the images need to be easily retrieved along with the numerical results. Measurement and analysis, database management, retrieval and statistical analysis of data, and data visualization need to be integrated to provide a process a researcher can use to answer questions quantitatively and efficiently.

In the present invention, a stain or a combination of stains are used as an agent to make features of a given tissue specimen visible to a human eye and or machine vision under certain magnifications. With reference to blood vessels, staining of elastin is key to the feature extraction. Feature extraction begins by identifying and labeling features of interest.

It is useful to briefly define restenosis, the impact it has on blood vessel geometry, and the visual appearance of the different features. In particular, we would like to point out the source of the textural differences between the types of tissue.

The pathobiology of restenosis is a multi-factorial process [Orford, J L, Selwyn, A P, Ganz, P, Popma, J J, and C. Rogers. The comparative pathobiology of atherosclerosis and restenosis. *Am J Cardiol* 86(4B): 6H–11H, Aug. 24, 2000.]. The process exhibits the characteristics of an inflammatory response to injury. Cytokines and adhesion molecules produced in this response recruit macrophages/monocytes and other inflammatory cells into the tunica media [Qiao, J H, Tripathi, J, Mishra, N K, et al. Role of macrophage colony-stimulating factor in atherosclerosis: Studies of osteopetrotic mice. *Am J Pathol* 150: 1687–99, 1997.]. This recruitment is an attempt to "heal" or remodel the wound. The macrophages produce metalloproteinases, protein-degrading enzymes, which break down the extracellular matrix proteins (e.g., collagen) compromising the structural integrity of the underlying endothelium [Galis, Z S, Sukhova, G K, Lark, M W, and P Libby. Increased expression of matrix metalloproteinases and matrix degrading activity in vulnerable regions of human atherosclerotic plaques. *J Clin Invest* 94: 2493–403, 1994.] When this happens, the underlying extracellular matrix is exposed to circulating coagulation factors and platelets. In particular, platelet adhesion causes the release of platelet-derived growth factor, which in turn stimulates the proliferation of the medial smooth muscle cells into the tunica intima.

The slides were stained with a combination of Verhoeff's elastin and Masson's Trichrome [Carson, F., Histotechnology, ASCP Press, Chicago, 1997] stains, which stain elastin and collagen respectively. The IEL and EEL stain black, collagen stains blue, and smooth muscle stains red. In our porcine model, the smooth muscle cells invading the tunica intima lack the connective tissue that is stained black. It therefore stains differently than the tunica media and tunica adventitia. As a result, the neointima tissue is differentiated texturally from the tunica media and tunica adventitia. Image processing can enhance the boundaries between these tissues. In the images studied, angioplasty has also resulted in the rupture of the internal elastic lamina in one or more places.

Capturing the Images

The images were captured from the standard video output of a Sony DKC-5ST CCD camera mounted on a Nikon Eclipse E600 microscope with a planar apo-epifluorescence objective (20×). Each image is an assembly of a montage of images with height by width dimensions of 300 microns×403 microns. Other suitable image sizes may be selected. The image resolution is 0.65 microns/pixel. A background image of a tissue-free area of the slide is captured before imaging each tissue sample to normalize for any changes in color or intensity of the incident light over time. The imaging system is also calibrated by imaging a microscopic grid to more precisely determine pixel resolution. Feature extraction and segmentation is dependent on accurate color and texture differentiation. Therefore, imaging of tissue is performed after making sure the background image intensity is not saturated.

The image shown in FIG. 1A is a cross-section of a normal artery showing the basic structure of the blood vessel. These basic structural features are lumen, intima, tunica media and tunica adventitia. The internal elastic lamina surrounds the thin layer of endothelial cells around the lumen, and cannot be seen clearly in this image. Note that the intensity of the image is saturated. The light intensity had been adjusted to permit an operator to comfortably view the image. This affects the quantitative repeatable measurement of color and therefore has an adverse effect on automated feature extraction. The image should not saturated for the automatic process of the invention. It may be saturated for manual measurements. FIG. 1B shows an image after analysis. In this image the internal elastic lamina was fractured. The feature boundaries have been outlined in the image, and the measurement and analysis results (discussed further elsewhere in this document) were imprinted on the image itself. Features of interest are the lumen, the internal elastic lamina, any fracture of the internal elastic lamina and the distance between the fractured ends, the tunica intima, the neointima, and the vessel perimeter defined by the inside edge of the EEL.

Extracting Features

The vessels that have been studied have all been injured by balloon angioplasty. The damage consists of one or more fractures of the internal elastic lamina, and subsequent restenosis-like response of the vessels by the proliferation of smooth muscle cells within the vessel boundary. These vessels do not have the geometry of a normal vessel with defined symmetric layers. Images of several vessels showing the variability in the shape of injured vessels that have been processed are shown in FIG. 2(A–H).

Features are extracted using three attributes: intensity, color, and morphology. The lumen and EEL are extracted first. The internal elastic lamina is then extracted using the constraint that it is located between these layers. Dark areas of the internal elastic lamina and the EEL are close in color. The Verhoeff's elastin stain absorbs all three color channels, in particular green light, so these regions appear black. The resulting color vector of these features is unique enough within the image to segment these regions.

Since there is no tissue within the area of the lumen, this area is unstained. The lumen area and boundary are extracted automatically using an optimal threshold determined from the intensity histogram of the grayscale image. The lumen is generally the largest object in the image with an intensity above the threshold that does not touch the edge of the image. However, there may be other blood vessels or tears in the tissue. If so, the user can be asked to indicate a point within the lumen to identify it as the object of interest. Extraneous islands of tissue within the lumen are filtered out using a morphological filling [User Guide, Image Processing Toolbox, The Mathworks Inc., 1997] operation to create one large connected lumen area.

The external elastic lamina is at the boundary between the tunica adventitia and the tunica media. To extract this feature, the user is asked to sample the color of a dark pixel within the tunica adventitia near the boundary. This pixel will have been stained by Verhhoeff's elastin stain and should correspond with the EEL. The expression $$D = \sqrt{(R-R_{EEL})^2 + (G-G_{EEL})^2 + (B-B_{EEL})^2} \quad (1)$$

is evaluated for every pixel in the image. R, G, and B refer to the red, green, and blue color channels. The subscript "EEL" refers to the external elastic lamina. D is the three-dimensional Euclidean distance in color space between the color of the sampled pixel in the tunica adventitia and each pixel in the image. Pixels within a threshold distance in this color space of the 3-D color of darkly stained tissue in the tunica adventitia are segmented from the image.

The pixels are connected into a contiguous region using several dilation operations. After these operations, the resulting region will be the largest single connected object in the image. The pixels that were the source for creating this large region, and are a subset of this region, are identified as belonging to the EEL. The inside boundary of the EEL is identified as being those points that are closest to the lumen. These points are identified as points on the vessel perimeter. The EEL may be incomplete and open because of the angioplasty procedure. The resulting gaps can be spanned with a section of an ellipse or a spline curve with minimal interaction from the user.

The internal elastic lamina is normally just beyond the thin endothelial layer bounding the lumen. The observed width is approximately 4 microns across. In an injured vessel, neointimal tissue proliferates between the internal elastic lamina and the lumen. In addition, the fractured ends of the internal elastic lamina separate away from each other. In addition to one or two major fractures, the internal elastic lamina is often comprised of short disconnected segments.

The stained internal elastic lamina does not have any particularly unique geometrical properties or color although it does stain darker than its surrounding tissue. To extract this feature the user is asked to sample the color of a pixel comprising the lamina, and the program identifies and highlights all other pixels in the image of similar color. For each of the highlighted pixels, D, as expressed by Equation 1, is less than a threshold value. Other connective tissue in the media and tunica adventitia is also stained, so this process must be followed by several morphological operations to extract the internal elastic lamina. To filter out extraneous objects, regions with a maximum width, minimum perimeter, and minimum area are extracted from the objects of specified color within the image [User Guide, Matrox Imaging Library, Matrox Electronic Systems Ltd., 1999]. Further morphological operations are used to connect segments into continuous larger sections. These larger objects between the lumen and the adventitia are selected to belong to the internal elastic lamina.

Figure 3A:
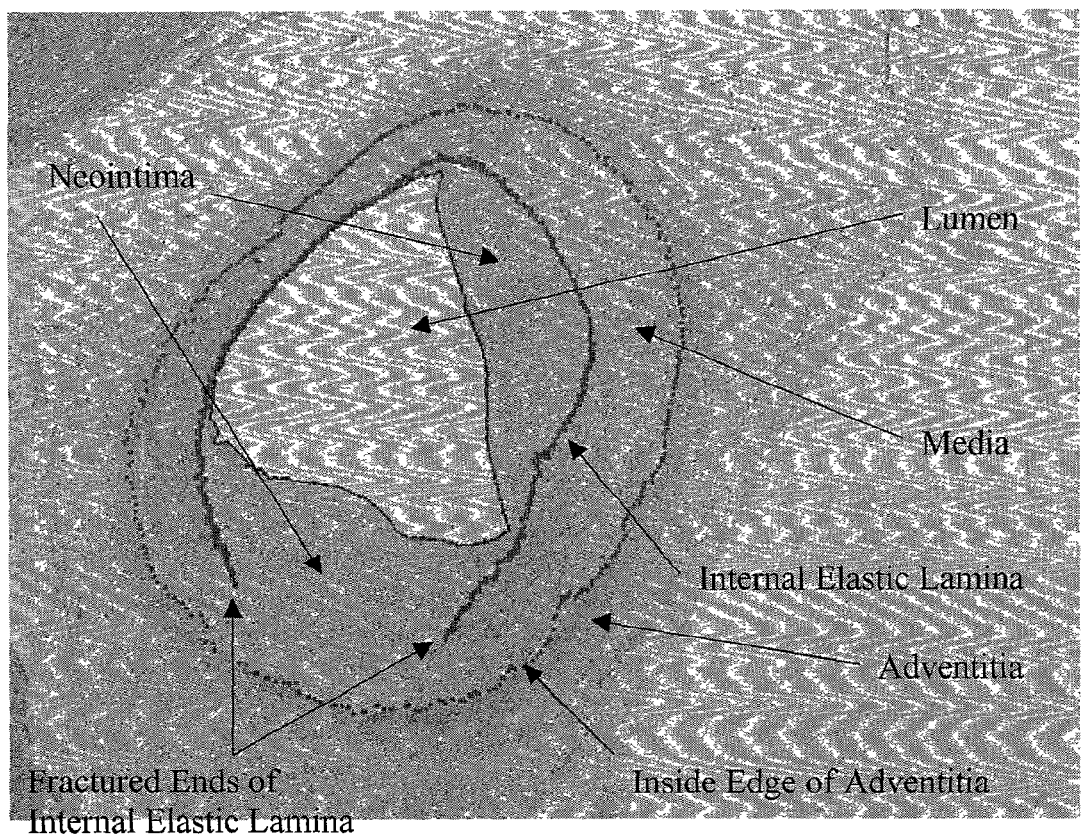
FIGS. 3A–3C depict automatically extracted features including the lumen boundary, the IEL, and the inside edge of the external elastic lamina (EEL).
Figure 3B:
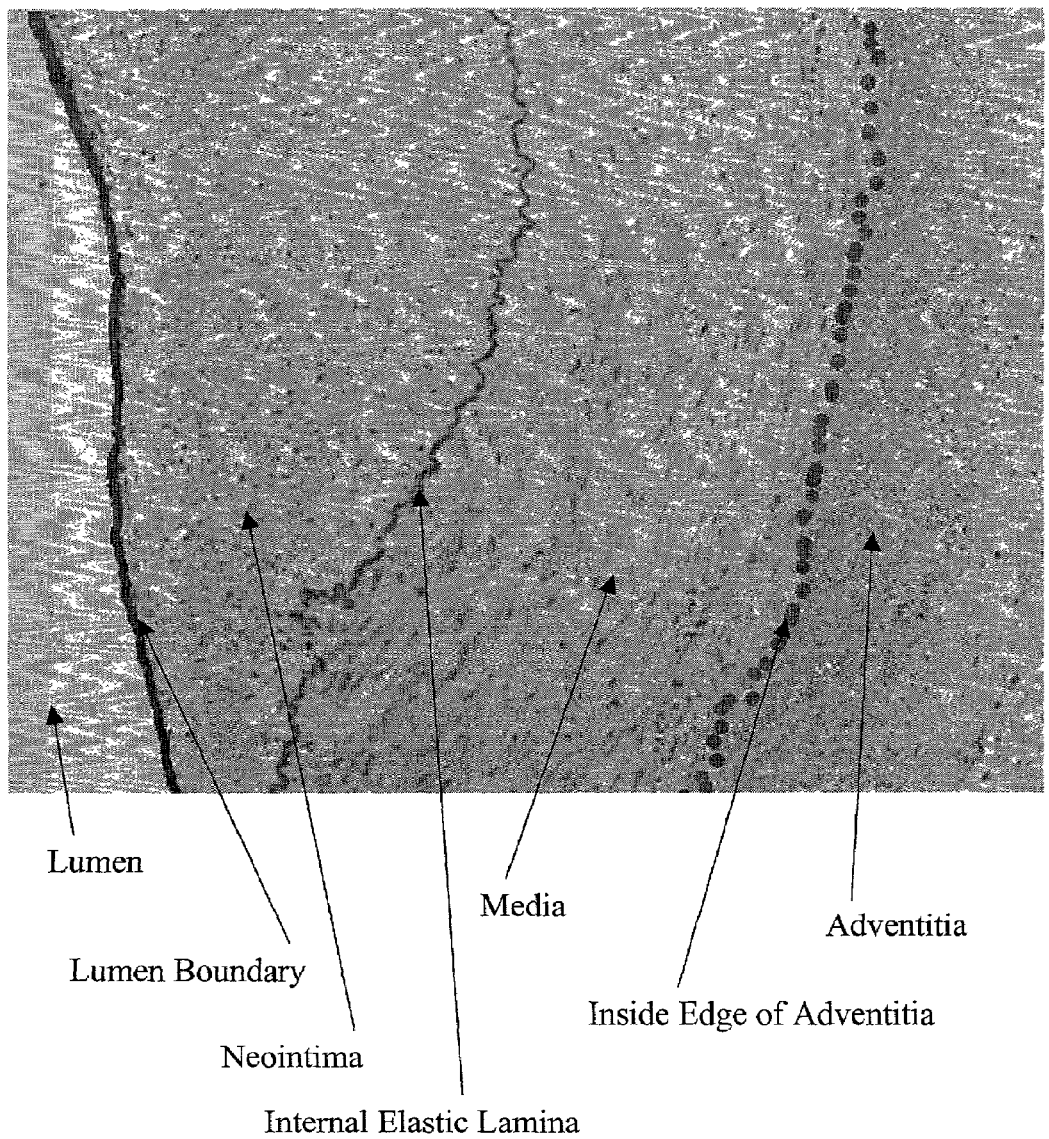
Figure 3C:
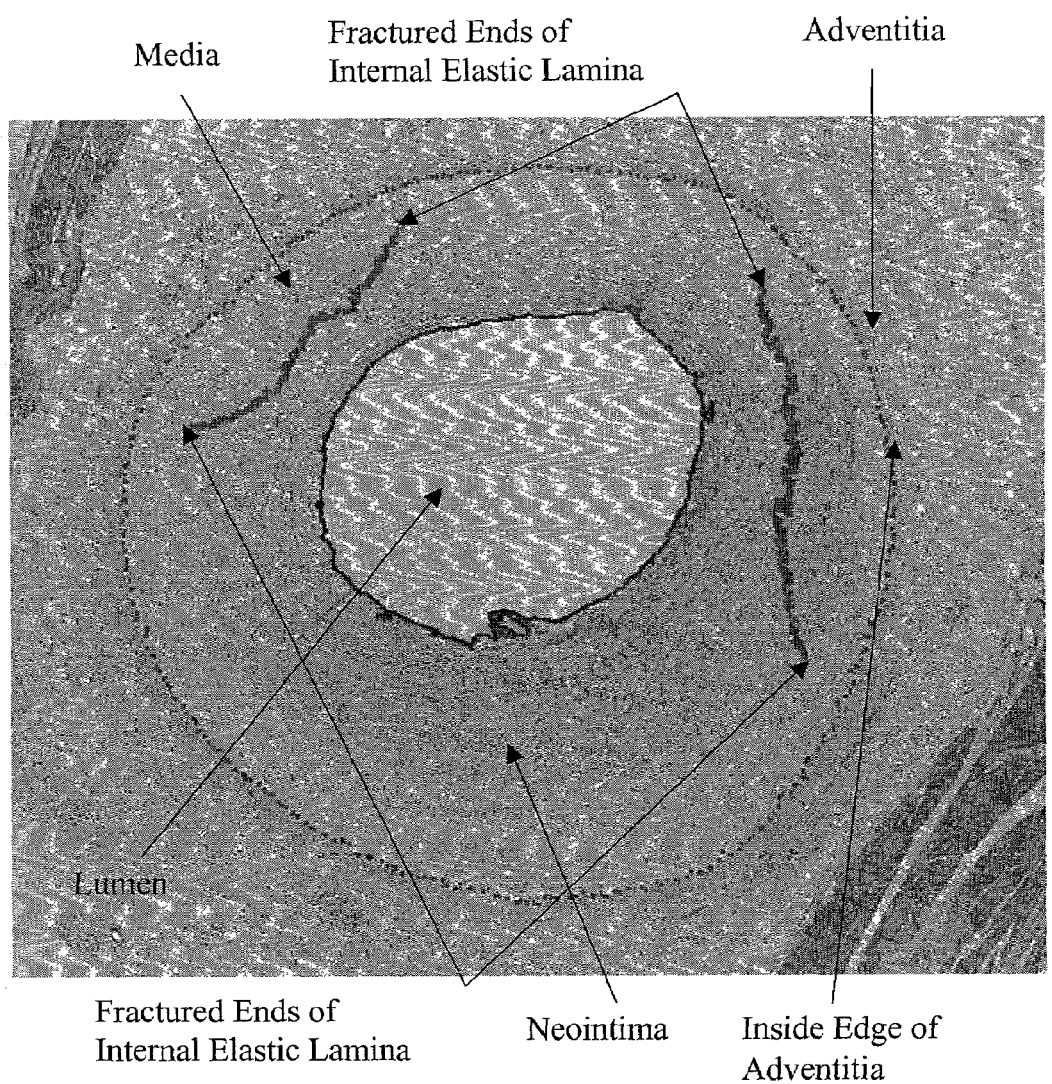

The perimeter of the lumen, the internal elastic lamina, and the external elastic lamina are extracted with minimal effort. The results are shown in FIGS. 3A–3C. The image in FIG. 3A shows a single fracture of IEL and FIG. 3B shows the higher resolution image of a part of the image 3A. FIG. 3C shows a double fracture of IEL. The coordinates of these features can now be extracted easily even at low resolution for further processing.

Figure 4A:
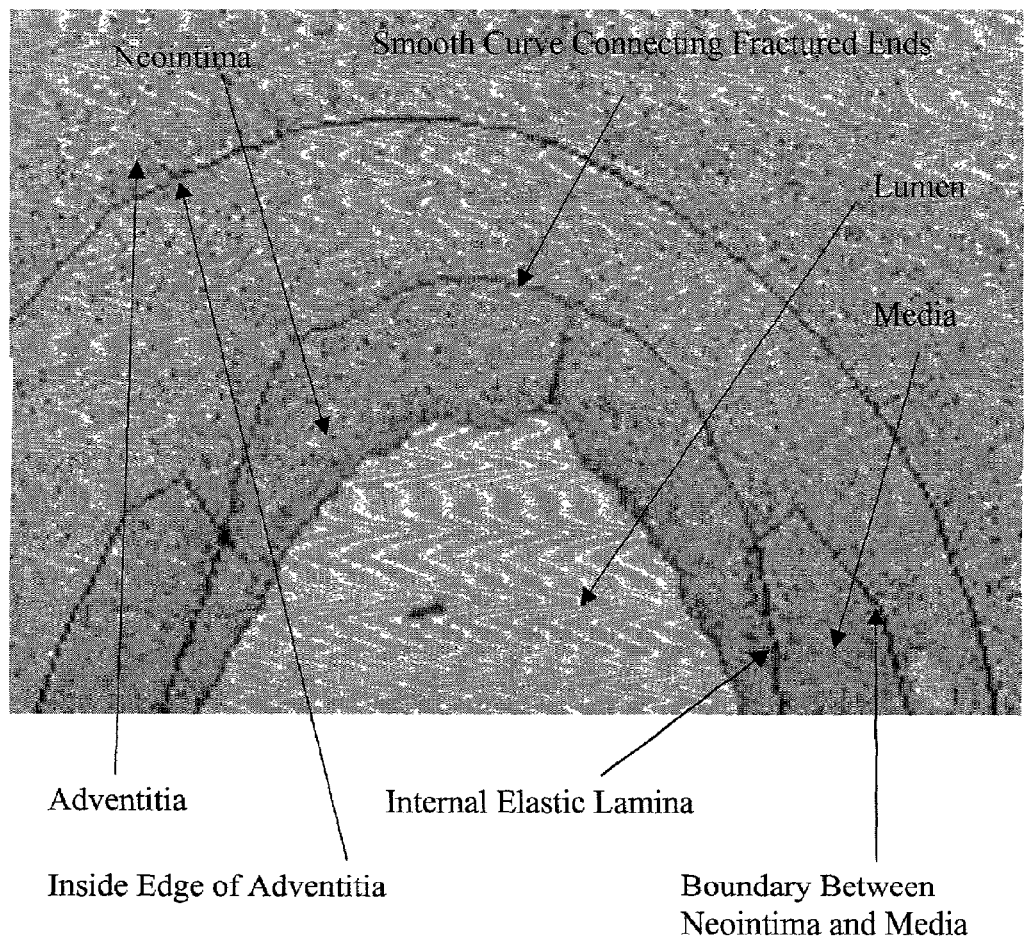
FIGS. 4A–4C illustrates images showing a contour, which was automatically generated, connecting the two ends of the broken TEL.
Figure 4B:
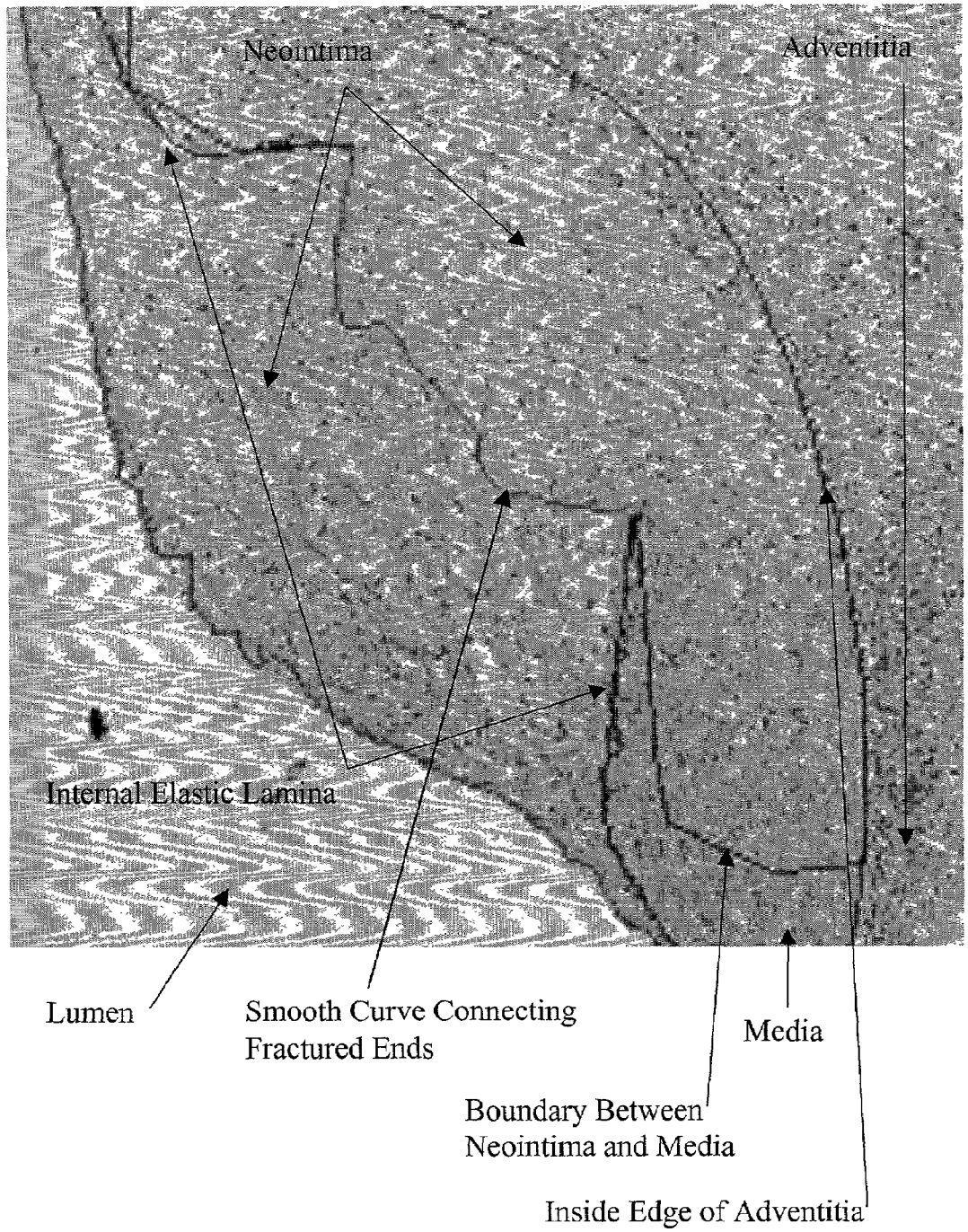
Figure 4C:
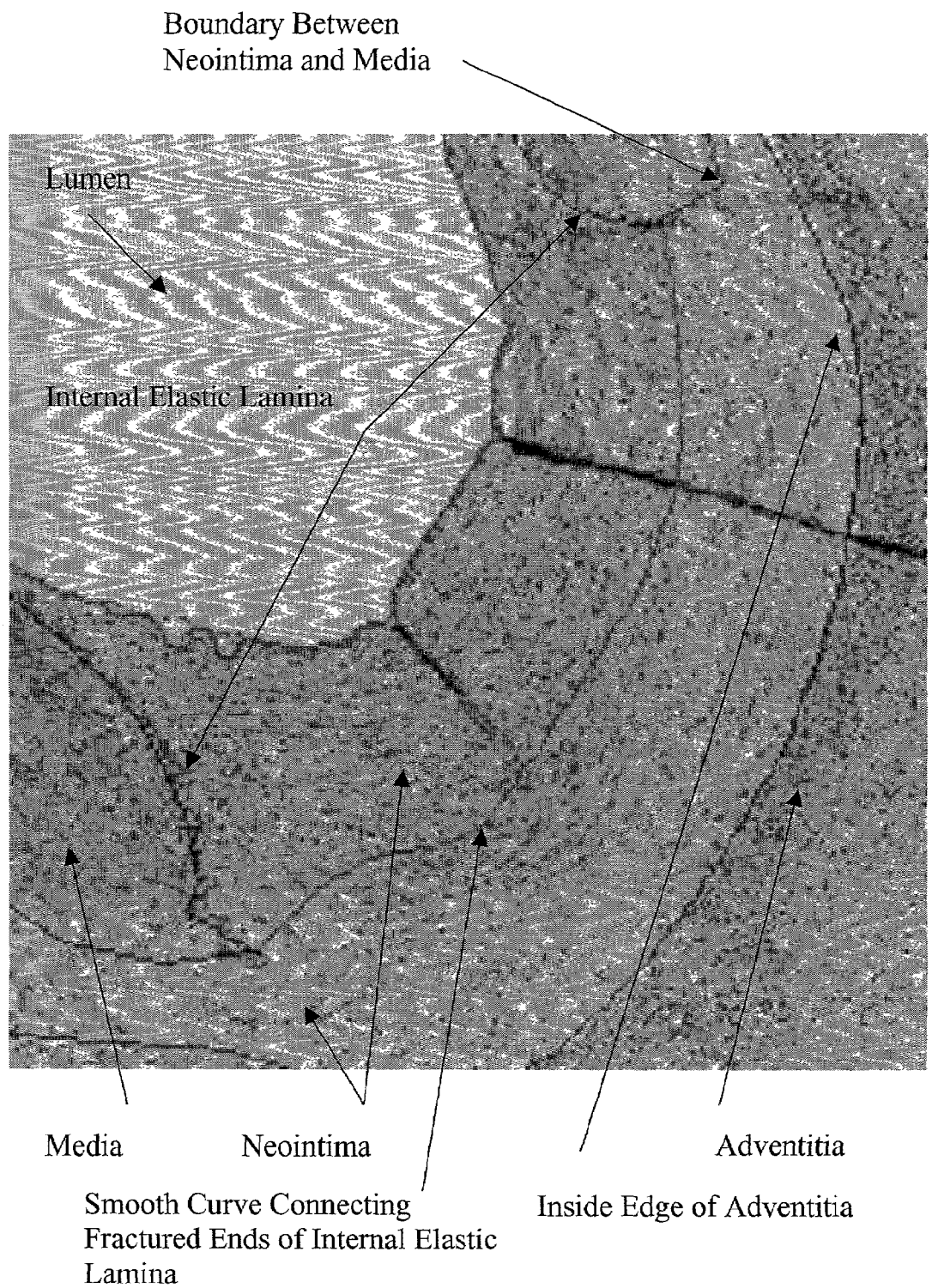

Two subjective measurements remain. The first is to determine the best way to draw a smooth curve between the fractured ends of the internal elastic lamina in order to determine the size of the separation. Each fractured end is a measurable distance away from both the lumen and the external elastic lamina. At each end these distances have specific ratios. As a curve is generated between one fractured end and the other, the condition that this ratio varies linearly from its value at one end to the other is enforced. Presented in FIG. 4(A-C) are images of different vessel cross sections each showing a contour that was automatically generated that connects the two ends of the broken internal elastic lamina. The size of the fracture as measured by the length of the contour is one of the parameters used to assess the restenosis-like response.

The second subjective measurement is the detection of the boundary between the neointima and the tunica media. This boundary may not be well defined. Instead, its visual appearance can vary slowly and continuously through the tissue.

Figure 5A:
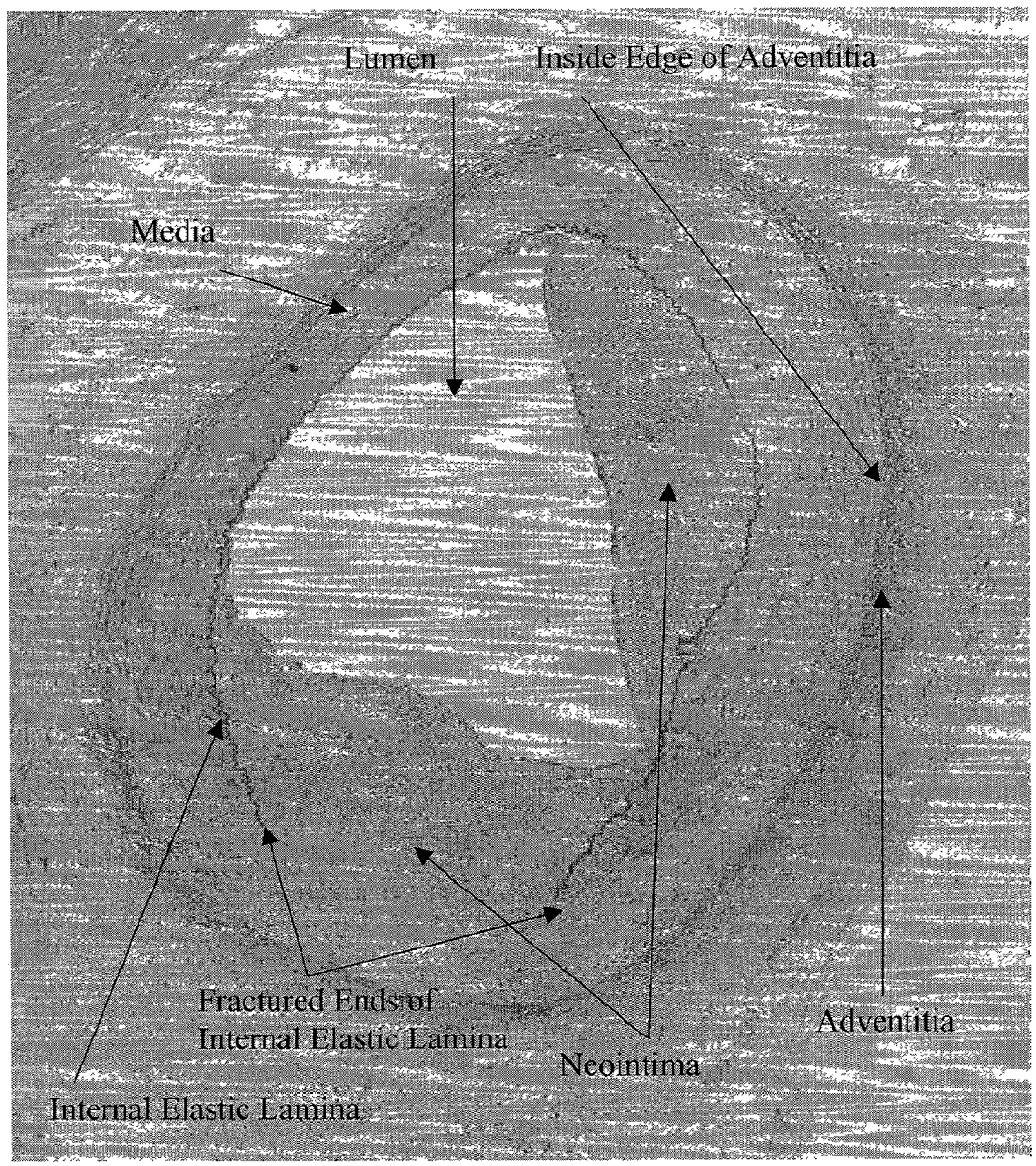
FIGS. 5A–5C illustrate images modified to have exponential histograms. The images of FIGS. 5D–5F are the same as (FIGS. 5A–5C) respectively, but are simply enhanced images created to provide higher contrast between tunica media and neointima.
Figure 5B:
Figure 5C:
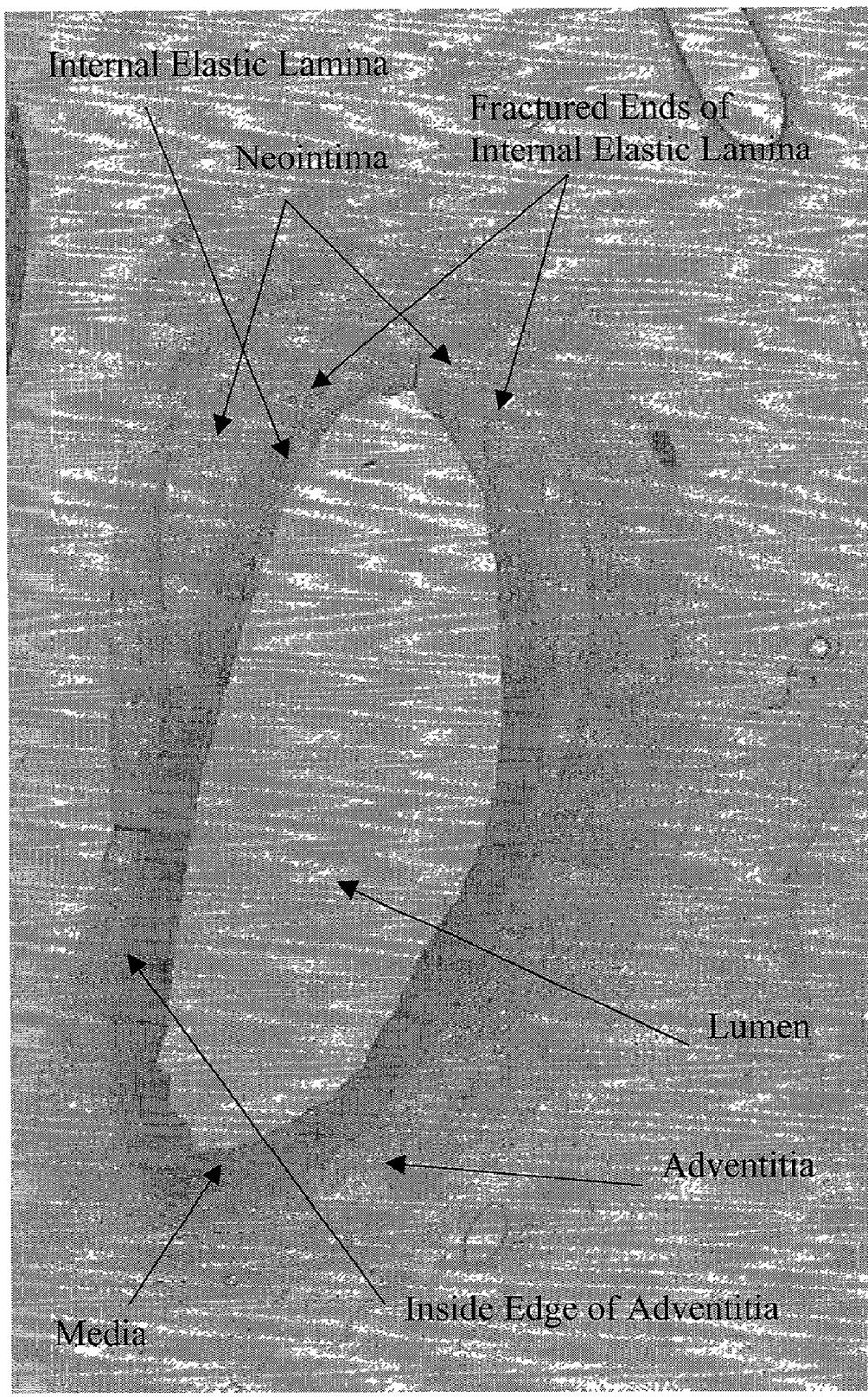
Figure 5D:
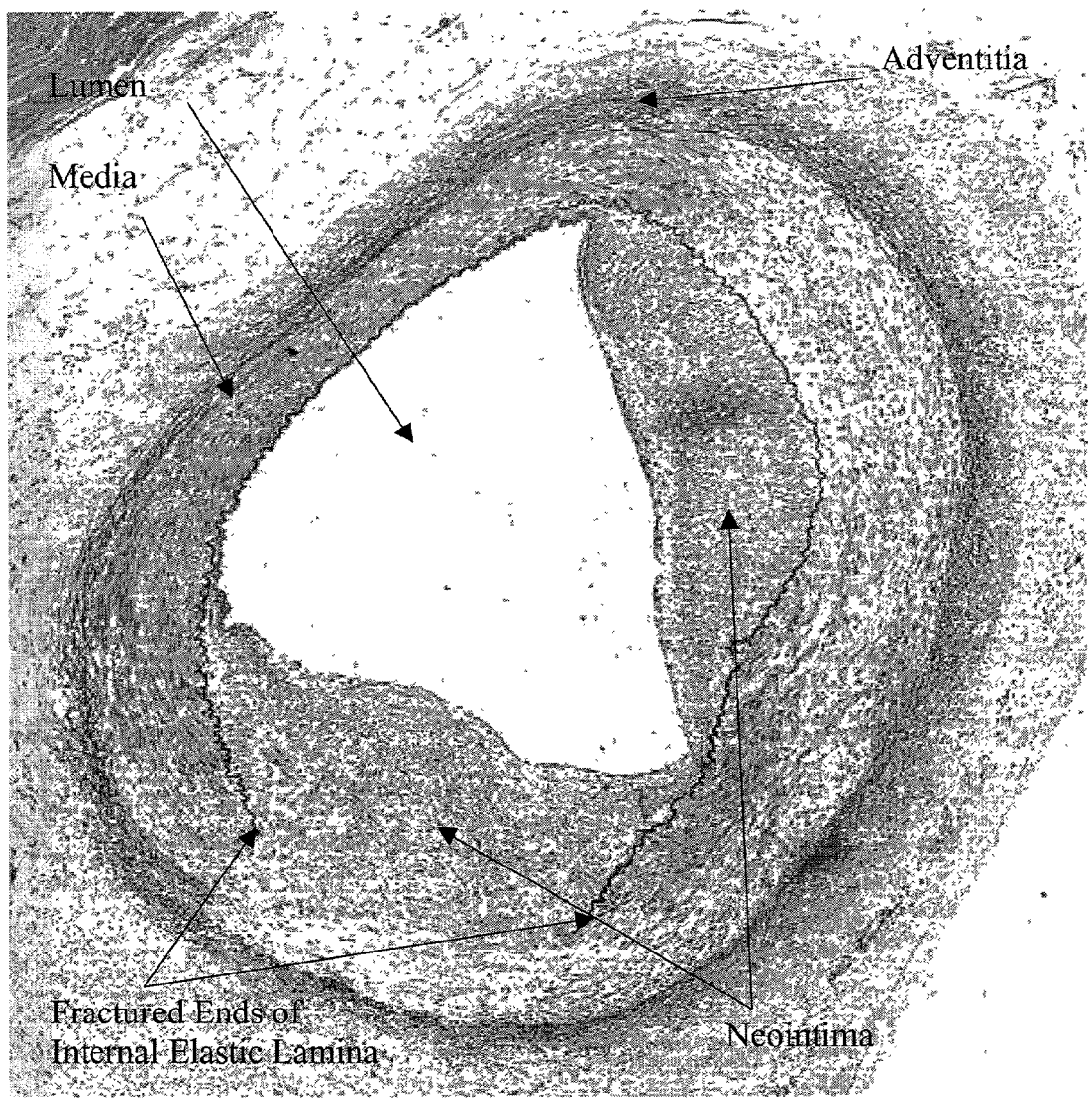
Figure 5E:
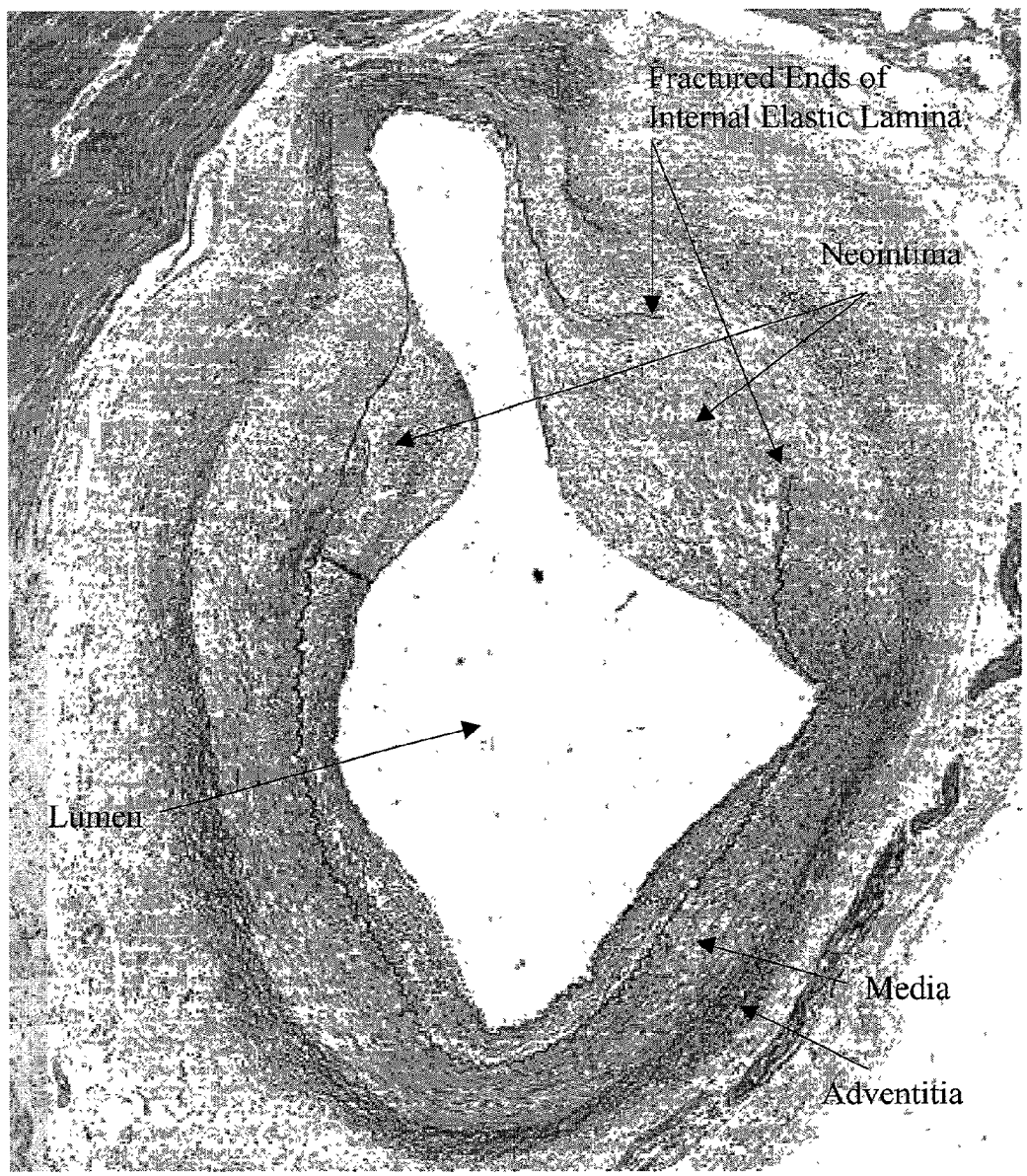
Figure 5F:
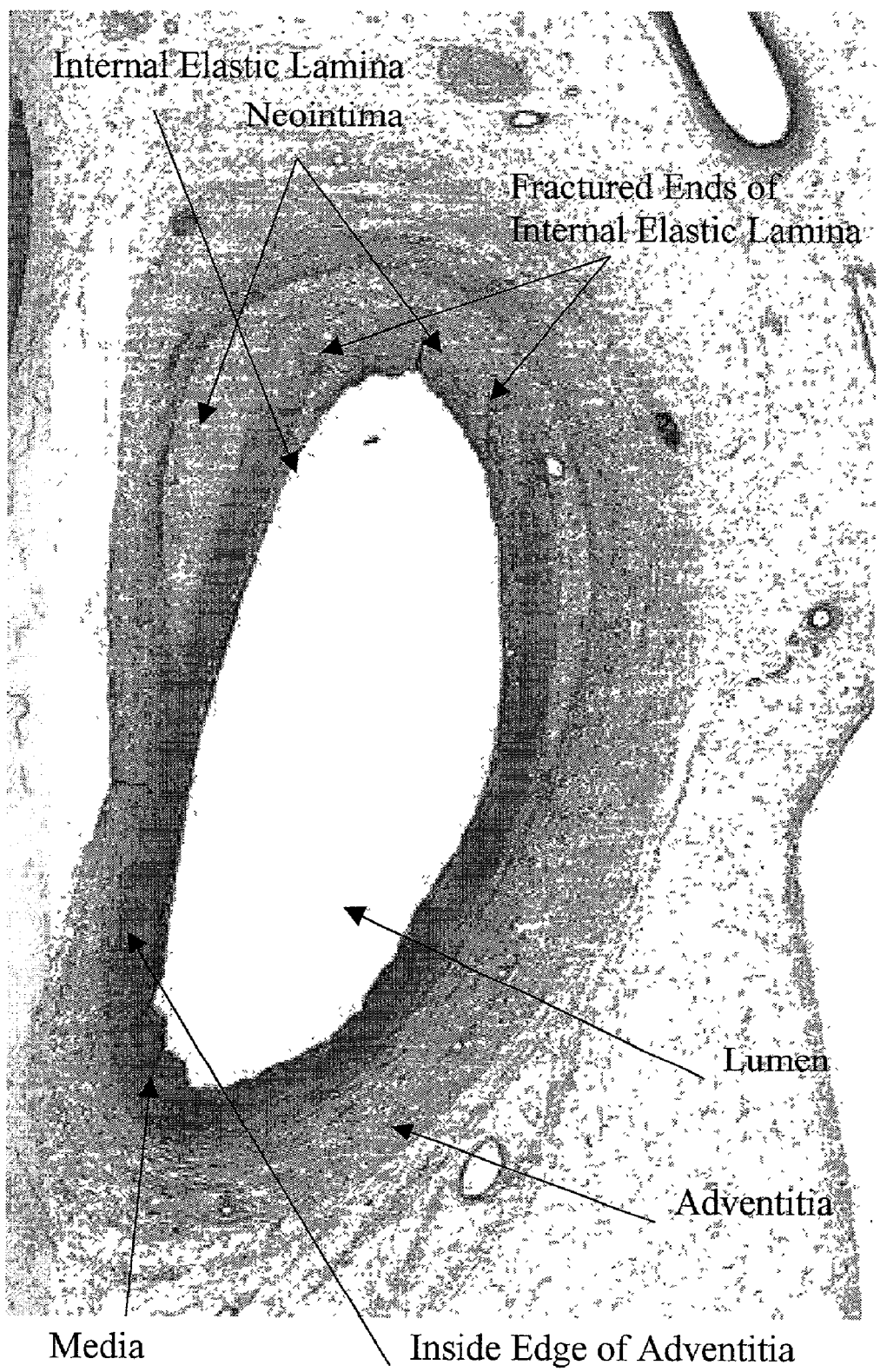

The neointima is composed of smooth muscles cells with little of the darkly stained connective tissue that is present in the tunica media. Modifying the image histogram [Pratt, W., Digital Image Processing, p. 275, Wiley Interscience, New York, 1991] can enhance image contrast. The intention is to determine if the image can be analyzed at a lower resolution without the need to pan and zoom, thereby increasing the speed and reducing the tedium of the measurement process. Images in FIGS. 5A–5F to show the increased contrast generated by creating images with exponential histograms within each color image plane to accentuate regions with different texture. More specifically, the images FIGS. 5A–5C were modified to have exponential histograms. The enhanced images of FIGS. 5A–5C are shown in FIGS. 5D–5F. They were created to provide higher contrast between tunica media and neointima.

In the paragraphs above, it was described how feature extraction has been automated to an extent. In addition, the image-processing capabilities of the analysis software have been augmented with tools common to computer-aided design (CAD) to further enhance and automate the measurement and analysis process. Tools that are common to CAD include the ability to pick points and group them, the ability to fit polynomial curves or splines to groups of points, and the ability to merge curve segments in an ordered fashion so they bound regions of interest.

The process for assembling points into groups through which curves will be fit is as follows. The user first identifies the feature of interest that is being extracted to the program, which in turn expects the user to extract the feature using a standard procedure. The user then manually traces feature boundaries. If the points chosen along the path defined by the user are within a threshold distance of the extracted points, the extracted points are used to compute a boundary curve. If the chosen points veer from the automatically extracted points, the boundary is modified to follow the chosen points. When the threshold is set to zero an outline of the feature is created without using any of the automatically extracted points, aside from the guidance they provided.

Tools are provided to enable a user to identify boundary segments in an order that circumscribes the boundaries of features of interest as opposed to circumscribing the entire feature in one procedure. When doing this, the beginning and end of the boundary segments need to be identified in a specific order to connect the boundary segments together. Additional tools are provided to enable the user needs to make corrections if the automatically extracted boundaries need adjustment.

The disconnected pieces of objects in the image may be joined into complete objects by other, related means. Rather than identifying a certain subset of all pixels as belonging to an object by merely applying a threshold, each pixel in an image may be assigned the probability of that point being part of an object to be identified. These probabilities are calculated from the image and from a knowledge of the particular image analysis problem under study. A threshold is next set, and those points with probabilities greater than the threshold are conditionally identified as being part of an object. Call this set of points the "conditional set". The probabilities at all points in the image are then updated, based on their proximity to the nearest point in the conditional set, with the probabilities being increased for points close to the set, and decreased for points far from the set. Thus, image points that are close to points in the set are now considered more likely to belong to an object, while points which are far from the conditional set are considered less likely to be part of an object. Once the probabilities have been updated, a new conditional set is found. The cycle is then repeated for a fixed number of iterations, or until convergence is achieved. Finally, those points with probabilities greater than the threshold are identified as being part of an object, while those with lower probabilities are not.

Measuring and Analyzing

Measurement and analysis has been developed independently of feature extraction to determine the following:
1. Perimeter of the adventitia.
2. The vessel perimeter. (Circumscribed inside edge of the external elastic lamina.)
3. Vessel area. (Area within the vessel perimeter.)
4. Lumen perimeter.
5. Lumen area.
6. Fracture length: arc length between fractured ends of internal elastic lamina drawn roughly equidistant between the external elastic lamina and the edge of the lumen.
7. Neointimal area: circumscribe the neointima being careful to exclude the lumen.
8. Medial area: computed as the vessel area minus the combined lumen and neointimal areas.

A set of ratio computed from these measurements provide more information for evaluating the extent of restenosis:
1. Fracture length/vessel perimeter or FL/VP.
2. Neointimal area/vessel area or IA/VA.
3. Neointimal area/medial area or IA/MA.
4. Ratio #2 divided by ratio #1 or (neointimal area/vessel area)/(fracture length/vessel perimeter) or (IA/VA)/(FL/VP).

The degree of restenosis may be determined from by knowing any one or more (of 1–4 above) of the set of ratios.

Figure 6A:
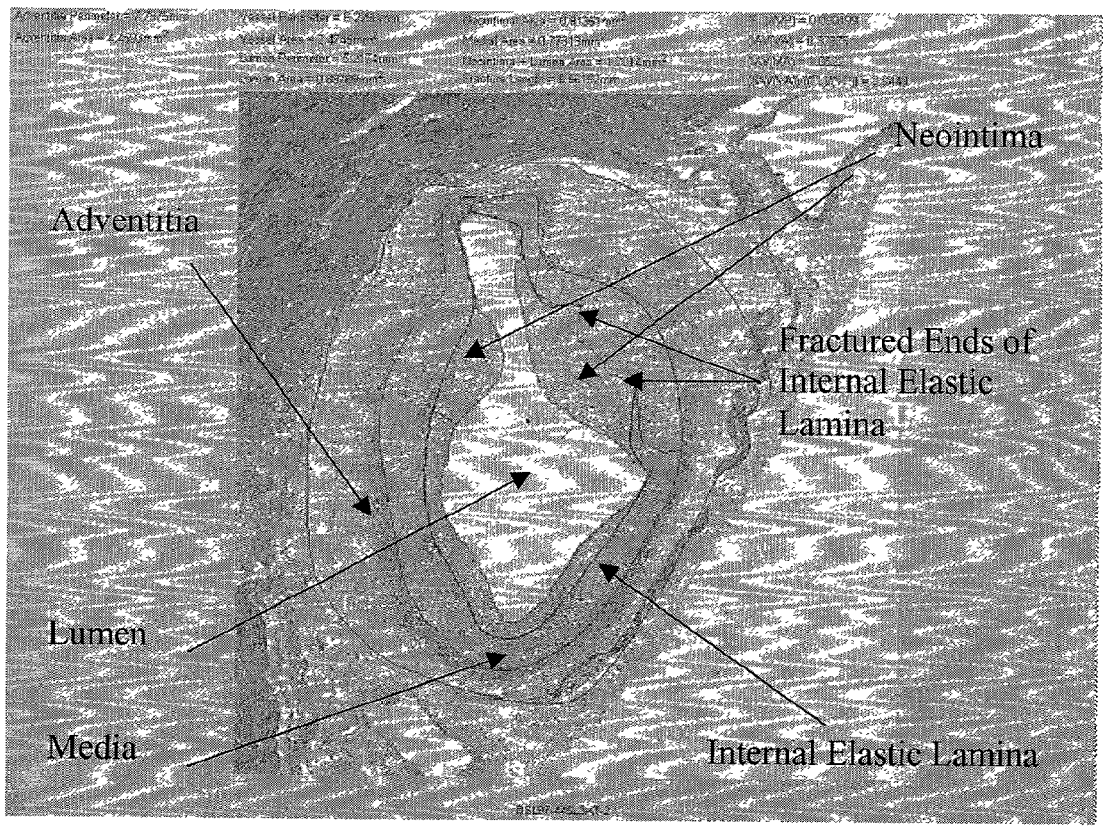
FIGS. 6A and 6B show images of cross sections of different vessels subject to measurement and analysis process.
Figure 6B:
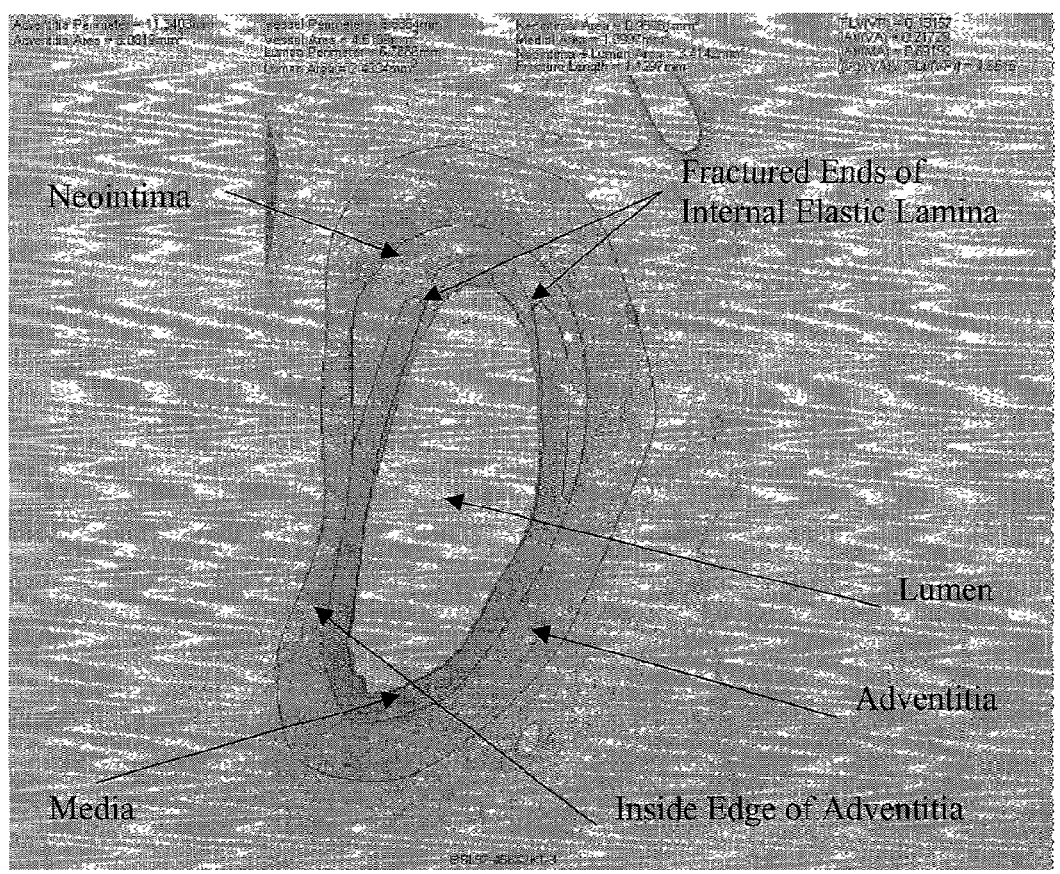

Determination of the vessel perimeter and lumen perimeter are usually automatic. If not, they can be defined manually. The neointima is bounded by the fractured internal elastic lamina, by a segment of the external elastic lamina, and by segments of the media boundary as shown in FIGS. 6A and 6B. The neointima shares a segment of the vessel perimeter. That particular segment should not need to be outlined twice, once as part of the vessel perimeter and once as part of the neointima boundary, as is done when the features are outlined manually without aid from the computer. It is for this reason the software is able to merge existing curve segments.

TABLE 1

The measurement and analysis results imprinted on the top portion of the images shown in FIGS. 6A and 6B are presented in this Table.

| Measurements | FIG. 6A | FIG. 6B |
| --- | --- | --- |
| Adventitia perimeter | 7.7975 mm | 11.3403 mm |
| Adventitia perimeter | 4.4593 mm$^2$ | 8.0819 mm$^2$ |
| Vessel perimeter | 6.2298 mm | 8.5864 mm |
| Vessel area | 2.4745 mm$^2$ | 4.5139 mm$^2$ |
| Lumen perimeter | 5.2174 mm | 6.7866 mm |
| Lumen area | 0.88789 mm$^2$ | 2.4334 mm$^2$ |
| Neointimal area | 0.81351 mm$^2$ | 0.98081 mm$^2$ |
| Medial area | 0.77313 mm$^2$ | 1.0997 mm$^2$ |
| Neointimal area + Lumen area | 1.7014 mm$^2$ | 3.4142 mm$^2$ |
| Fracture length | 0.56192 mm | 1.1297 mm |
| FL/VP | 0.090199 | 0.13157 |
| IA/VA | 0.32875 | 0.21729 |
| IA/MA | 1.0522 | 0.89192 |
| (IA/VA)/(FL/VP) | 3.6448 | 1.6515 |

Including in a Database

More often than not, images and data are stored separately. The data may be kept in spreadsheets where it is not easily accessible, efficiently analyzed or shared. Similarly, the images are accessible separately through the operating system. In principle, the images and data can be merged using hyperlinks. From a practical standpoint, a more robust database that manages the input and retrieval of data and images is needed to compare studies taking place at different times, with different protocols, and with measurements made by different systems. The database needs to have sufficient and accurate information to enable the user to normalize the results to make meaningful comparison between studies.

The analysis of individual tissue sections is not of much value unless the results can be compared within and across experimental studies. As an example, consider the following therapeutic approaches being examined to prevent restenosis:

1. Brachytherapy or transient exposure to either beta or gamma radiation (Tierstein, P S. Gamma versus beta radiation for the treatment of restenosis (Editorial). *Herz* 23: 335–6, 1998) has been shown to reduce restenosis from 45% to 12%.
2. New stent design (Rogers, C, Tseng, D Y, Squire, J C, and E R Edelman. Balloon-artery interactions during stent placement: A finite element analysis approach to pressure, compliance, and stent design as contributors to vascular injury. *Circ Res* 84: 378–83, 1999), which preserves the endothelium or cells lining the lumen, appears critical.
3. Distal protection devices placed downstream of the stent collect debris to prevent embolisms or blood clots from causing ischemia or infarctions.
4. Stent coatings that prevent neointimal proliferation (Fischell, T A. Polymer coatings for stents. Can we judge a stent by its cover? (Editorial). *Circulation* 94: 1494–5, 1996).
5. Novel catheters that minimize vascular perturbation and enhance diagnostics and therapeutics.
6. Photodynamic chemotherapy that reduces inflammation (Pollock, M E, Eugene, J, Hammer-Wilson, M, and M W Bems. Photosensitization of experimental atheromas by porphyrins. *J Am Coll Cardiol* 9: 639–46, 1987; Michaels, J A. The accumulation of porphyrins in atheroma: Potential for diagnosis and treatment? *J Photochem Photobiol B* 2: 134–7, 1988; Allison, B A, Crespo, M T, Jain, A K, Richter, A M, Hsiang, Y N, and J G Levy. Delivery of benzoporphyrin derivative, a photosensitizer, into atherosclerotic plaque of Watanabe heritable hyperlipidemic rabbits and balloon-injured New Zealand rabbits. *Photochem Photobiol* 65: 877–83, 1997; Hsiang, Y N, Crespo, M T, Richter, A M, Jain, A K, Fragoso, M, and J G Levy. In vitro and in vivo uptake of benzoporphyrin derivative into human and miniswine atherosclerotic plaque. *Photochem Photobiol* 57: 670–4, 1993).

7. Diet and lipid/cholesterol lowering regimens.

The present invention provides that information from all studies such as these would be input into a shareable database that could be queried in a way that enables researchers to draw conclusions and make predictions.

The images and the output of the analysis results that have been presented have been input into a relational database that provides query tools, advanced analysis tools, data visualization capabilities, and web access. Genetic, mechanical, and clinical information can also be extracted from the tissue for the purpose of correlating this additional information with the structural information extracted through image processing. A perpetual, shared, database that can be queried for statistical analysis provides a resource where data and images are organized that is important for quantitatively comparing the differences in effects seen between studies.

Summary of Blood Vessel Embodiment

A measurement and analysis system that was developed to be a tool for pathologists to quantitatively evaluate blood vessel shape while reducing the tedium involved in making manual measurements has been described. The entire process is composed of several steps. Though not discussed in this disclosure, image capture requires the assembly of a montage of multiple images, each of which requires focusing before image capture. After assembling the image, features of interest including the lumen, neointima, internal elastic lamina, tunica media, external elastic lamina and tunica adventitia are identified and the boundaries of these features extracted. Vessel geometry must be analyzed at several resolution scales requiring zooming and panning. The extracted features are then analyzed to characterize the geometry of the vessel. Finally, these results and the images are input into a database for easy retrieval and statistical analysis.

The emphasis in this disclosure has been on feature extraction and geometric analysis. Structures such as the lumen, internal elastic lamina, external elastic lamina, and adventitia are first segmented using a combination of grayscale, color, and morphological operations. The boundaries of the extracted features are overlaid on the image enabling a pathologist to use the computed coordinates, or to outline features of interest manually. The pathologist still decides where feature boundaries are located but is relieved of the need to work intensively with the images. Finally, the results are input into a relational database for comparison with accumulated results and the results of other studies. This process effectively merges computer aided design, image processing and analysis to relieve the tedium of both the measurement process and the archiving of results.

References in Blood Vessel Embodiment

1. Orford, J L, Selwyn, A P, Ganz, P, Popma, J J, and C. Rogers. The comparative pathobiology of atherosclerosis and restenosis. *Am J Cardiol* 86(4B): 6H–11H, Aug. 24, 2000.
2. Qiao, J H, Tripathi, J, Mishra, N K, et al. Role of macrophage colony-stimulating factor in atherosclerosis: Studies of osteopetrotic mice. *Am J Pathol* 150: 1687–99, 1997.
3. Galis, Z S, Sukhova, G K, Lark, M W, and P Libby. Increased expression of matrix metalloproteinases and matrix degrading activity in vulnerable regions of human atherosclerotic plaques. *J Clin Invest* 94: 2493–403, 1994.
4. Carson, F., Histotechnology, ASCP Press, Chicago, 1997.
5. User Guide, Matrox Imaging Library, Matrox Electronic Systems Ltd., 1999.
6. User Guide, Image Processing Toolbox, The Mathworks Inc., 1997
7. Pratt, W., Digital Inage Processing, p. 275, Wiley Interscience, New York, 1991.
8. Tierstein, P S. Gamma versus beta radiation for the treatment of restenosis (Editorial). *Herz* 23: 335–6, 1998.
9. Rogers, C, Tseng, D Y, Squire, J C, and E R Edelman. Balloon-artery interactions during stent placement: A finite element analysis approach to pressure, compliance, and stent design as contributors to vascular injury. *Circ Res* 84: 378–83, 1999.
10. Fischell, T A. Polymer coatings for stents. Can we judge a stent by its cover? (Editorial). *Circulation* 94: 1494–5, 1996.
11. Pollock, M E, Eugene, J, Hammer-Wilson, M, and M W Bems. Photosensitization of experimental atheromas by porphyrins. *J Am Coll Cardiol* 9: 639–46, 1987.
12. Michaels, J A. The accumulation of porphyrins in atheroma: Potential for diagnosis and treatment? *J Photochem Photobiol B* 2: 134–7, 1988.
13. Allison, B A, Crespo, M T, Jain, A K, Richter, A M, Hsiang, Y N, and J G Levy. Delivery of benzoporphyrin derivative, a photosensitizer, into atherosclerotic plaque of Watanabe heritable hyperlipidemic rabbits and balloon-injured New Zealand rabbits. *Photochem Photobiol* 65: 877–83, 1997.
14. Hsiang, Y N, Crespo, M T, Richter, A M, Jain, A K, Fragoso, M, and J G Levy. In vitro and in vivo uptake of benzoporphyrin derivative into human and miniswine atherosclerotic plaque. *Photochem Photobiol* 57: 670–4, 1993.

All publications and references, including but not limited to patent applications, cited in this specification, are herein incorporated by reference in their entirety as if each individual publication or reference were specifically and individually indicated to be incorporated by reference herein as being fully set forth.

The preferred embodiments description herein is provided to enable any person skilled in the art to make and use the present invention. The various modifications to these embodiments will be readily apparent to those skilled in the art, and the generic principles defined herein may be applied to other embodiments without the use of the inventive faculty. Thus, the present invention is not intended to be limited to the embodiments shown herein but is to be accorded the widest scope consistent with the principles and novel features disclosed herein. Accordingly, this invention includes all modifications encompassed within the spirit and scope of the invention as defined by the claims.

What is claimed is:

1. A method for quantitative determination of overall shape of a blood vessel and the spatial relationship of different structures within a given blood vessel comprising the steps of:

(a) imaging a stained histological cross section of the given blood vessel to capture an image;

(b) automatically extracting features of the image to identify different boundary segments based on intensity, color and morphology of the image, wherein the boundary segments include the lumen boundary segment;

(c) applying image processing algorithms and computing boundary segment perimeters and areas after step (b); and (d) determining the blood vessel overall shape and spatial relationship of different structures within the blood vessel based on the boundary segment perimeters and areas.

2. The method of claim 1, wherein different boundary segments comprise adventitia, media, internal elastic lamina and intima.

3. The method of claim 1, wherein the boundary segment perimeters comprise perimeter of the vessel, adventitia, media and lumen.

4. The method of claim 1, wherein the boundary segment areas comprise area of the vessel, lumen, media and neointima.

5. The method of claim 1 wherein the computed boundary segment perimeters and areas are imprinted such that the perimeters and areas are viewed as part of the image.

* * * * *